(12) United States Patent
Viola et al.

(10) Patent No.: US 11,054,396 B2
(45) Date of Patent: Jul. 6, 2021

(54) HEMOSTASIS ANALYZER

(71) Applicant: HEMOSONICS LLC, Charlottesville, VA (US)

(72) Inventors: Francesco Viola, Charlottesville, VA (US); William F. Walker, Charlottesville, VA (US)

(73) Assignee: HEMOSONICS LLC, Charlottesville, VA (US)

( * ) Notice: Subject to any disclaimer, the term of this patent is extended or adjusted under 35 U.S.C. 154(b) by 0 days.

(21) Appl. No.: 15/169,036

(22) Filed: May 31, 2016

(65) Prior Publication Data
US 2016/0377577 A1 Dec. 29, 2016

Related U.S. Application Data

(63) Continuation of application No. 13/475,347, filed on May 18, 2012, now abandoned.

(60) Provisional application No. 61/488,046, filed on May 19, 2011.

(51) Int. Cl.
*G01N 29/024* (2006.01)
*G01N 29/22* (2006.01)
*G01N 33/86* (2006.01)

(52) U.S. Cl.
CPC ......... *G01N 29/024* (2013.01); *G01N 29/222* (2013.01); *G01N 33/86* (2013.01); *G01N 2291/02466* (2013.01); *G01N 2291/02818* (2013.01); *G01N 2291/02827* (2013.01); *G01N 2291/044* (2013.01); *G01N 2291/101* (2013.01)

(58) Field of Classification Search
CPC ..................................................... G01N 33/86
See application file for complete search history.

(56) References Cited

U.S. PATENT DOCUMENTS

| 3,876,379 A | 4/1975 | Ghim |
| 4,112,740 A | 9/1978 | Brandestini |
| 4,558,589 A * | 12/1985 | Hemmes ............... G01N 29/036 374/23 |

(Continued)

FOREIGN PATENT DOCUMENTS

| AU | 2011237383 | 7/2014 |
| CN | 1816306 | 8/2006 |

(Continued)

OTHER PUBLICATIONS

US 6,135,954 A, 10/2000, Cohen et al. (withdrawn)

(Continued)

*Primary Examiner* — Matthew D Krcha
(74) *Attorney, Agent, or Firm* — Meunier Carlin & Curfman LLC

(57) ABSTRACT

Provided are devices, systems and methods for the use of a portable unit for the evaluation of hemostasis. For example, a portable system for determining a plurality of hemostatic parameters may be included. The system includes a blood sample receptacle, an analyzer and a housing. The blood sample receptacle is configured to hold at least one blood sample. The analyzer is configured to determine at least two hemostatic parameters of the at least one blood sample. The housing is configured to operably couple the blood sample receptacle and the analyzer. The housing is portable and may, for example, have a thickness of 17.5 cm or smaller.

20 Claims, 17 Drawing Sheets

(56) References Cited

U.S. PATENT DOCUMENTS

| | | | |
|---|---|---|---|
| 4,695,956 A | 9/1987 | Leveen et al. |
| 4,705,756 A | 11/1987 | Spillert et al. |
| 4,756,884 A | 7/1988 | Hillman et al. |
| 4,814,247 A | 3/1989 | Spillert et al. |
| 4,849,340 A | 7/1989 | Oberhardt |
| 4,852,577 A | 8/1989 | Smith et al. |
| 4,900,679 A | 2/1990 | Spillert et al. |
| 5,016,469 A | 5/1991 | Henderson et al. |
| 5,036,286 A | 7/1991 | Holm-Kennedy |
| 5,056,357 A | 10/1991 | Dymling et al. |
| 5,091,304 A | 2/1992 | La Duca et al. |
| 5,104,975 A | 4/1992 | McCormick et al. |
| 5,204,525 A | 4/1993 | Hillman et al. |
| 5,205,159 A | 4/1993 | Carr, Jr. |
| 5,234,839 A | 8/1993 | McCormick et al. |
| 5,273,517 A | 12/1993 | Barone et al. |
| 5,311,908 A | 3/1994 | Barone et al. |
| 5,331,964 A | 7/1994 | Trahey et al. |
| 5,473,536 A | 12/1995 | Wimmer |
| 5,487,387 A | 1/1996 | Trahey et al. |
| RE35,171 E | 3/1996 | McCormick et al. |
| 5,504,011 A | 4/1996 | Gavin et al. |
| 5,534,226 A | 7/1996 | Gavin et al. |
| 5,605,154 A | 2/1997 | Ries et al. |
| 5,606,971 A | 3/1997 | Sarvazyan et al. |
| 5,629,209 A * | 5/1997 | Braun, Sr. ............ G01N 11/105 |
| | | | 422/547 |
| 5,655,535 A | 8/1997 | Friemel et al. |
| 5,657,760 A | 8/1997 | Ying et al. |
| 5,673,699 A | 10/1997 | Trahey et al. |
| 5,744,898 A | 4/1998 | Smith et al. |
| 5,777,215 A | 7/1998 | Calatzis et al. |
| 5,800,781 A | 9/1998 | Gavin et al. |
| 5,810,731 A | 9/1998 | Sarvazyan et al. |
| 5,854,423 A | 12/1998 | Venegas |
| 5,888,826 A | 3/1999 | Ostgaard et al. |
| 5,899,861 A | 5/1999 | Friemel et al. |
| 5,921,928 A | 7/1999 | Greenleaf et al. |
| 5,952,560 A | 9/1999 | Collings et al. |
| 6,016,712 A | 1/2000 | Warden et al. |
| 6,039,691 A | 3/2000 | Walker et al. |
| 6,046,051 A | 4/2000 | Jina |
| 6,083,159 A | 7/2000 | Driscoll, Jr. et al. |
| 6,114,135 A | 9/2000 | Goldstein |
| 6,117,081 A | 9/2000 | Jago et al. |
| 6,135,957 A | 10/2000 | Cohen et al. |
| 6,200,532 B1 * | 3/2001 | Wu ............ G01N 29/036 |
| | | | 422/73 |
| 6,213,950 B1 | 4/2001 | Cespedes et al. |
| 6,221,672 B1 | 4/2001 | Baugh et al. |
| RE37,171 E | 5/2001 | Busche et al. |
| 6,225,126 B1 | 5/2001 | Cohen et al. |
| 6,232,127 B1 | 5/2001 | Lane et al. |
| 6,264,609 B1 | 7/2001 | Herrington et al. |
| 6,270,459 B1 | 8/2001 | Konofagou et al. |
| 6,277,074 B1 | 8/2001 | Chaturvedi et al. |
| 6,283,917 B1 | 9/2001 | Jago et al. |
| 6,318,191 B1 | 11/2001 | Chen |
| 6,371,912 B1 | 4/2002 | Nightinggale et al. |
| 6,402,704 B1 | 6/2002 | McMorrow |
| 6,412,344 B1 | 7/2002 | Danicich et al. |
| 6,436,722 B1 | 8/2002 | Clark et al. |
| 6,451,610 B1 | 9/2002 | Gorman et al. |
| 6,454,714 B1 | 9/2002 | Ng et al. |
| 6,494,834 B2 | 12/2002 | Konofagou et al. |
| 6,508,768 B1 | 1/2003 | Hall et al. |
| 6,514,204 B2 | 2/2003 | Alam et al. |
| 6,535,835 B1 | 3/2003 | Rubin et al. |
| 6,537,819 B2 | 3/2003 | Cohen et al. |
| 6,573,104 B2 | 6/2003 | Carr, Jr. et al. |
| 6,613,286 B2 | 9/2003 | Braun et al. |
| 6,613,573 B1 | 9/2003 | Cohen |
| 6,632,678 B2 | 10/2003 | Aiken et al. |
| 6,685,646 B2 | 2/2004 | Cespedes et al. |
| 6,687,625 B2 | 2/2004 | Srinivasan et al. |
| 6,692,439 B1 | 2/2004 | Walker et al. |
| 6,716,168 B2 | 4/2004 | Nock et al. |
| 6,726,629 B1 | 4/2004 | Frinking et al. |
| 6,750,053 B1 | 6/2004 | Widrig et al. |
| 6,764,448 B2 | 7/2004 | Trahey et al. |
| 6,787,363 B2 | 9/2004 | Cohen et al. |
| 6,797,519 B2 | 9/2004 | Cohen et al. |
| 6,890,299 B2 | 5/2005 | Cohen et al. |
| 6,951,544 B2 | 10/2005 | Trahey et al. |
| 7,179,652 B2 | 2/2007 | Cohen et al. |
| 7,192,726 B1 | 3/2007 | Carr, Jr. et al. |
| 7,202,048 B2 | 4/2007 | Carr, Jr. |
| 7,207,939 B2 | 4/2007 | Husher |
| 7,247,488 B2 | 7/2007 | Ghai et al. |
| 7,261,861 B2 | 8/2007 | Kautzky |
| 7,374,538 B2 | 5/2008 | Nightingale et al. |
| 7,399,637 B2 | 7/2008 | Wright et al. |
| 7,422,905 B2 | 9/2008 | Clague et al. |
| 7,439,069 B2 | 10/2008 | Nippoldt et al. |
| 7,524,670 B2 | 4/2009 | Cohen et al. |
| 7,674,616 B2 | 3/2010 | Farnam, III et al. |
| 7,732,213 B2 | 6/2010 | Cohen et al. |
| 7,879,615 B2 | 2/2011 | Kautzky |
| 7,892,188 B2 | 2/2011 | Walker et al. |
| 7,912,661 B2 | 3/2011 | Zeng |
| 7,972,271 B2 | 7/2011 | Johnson et al. |
| 8,058,023 B2 | 11/2011 | Gurbel |
| 8,110,392 B2 | 2/2012 | Battrell et al. |
| 8,236,568 B2 | 8/2012 | Kautzky |
| 8,372,343 B2 | 2/2013 | Goldstein |
| 8,548,759 B2 | 10/2013 | Walker et al. |
| 8,740,818 B2 | 6/2014 | Walker et al. |
| 9,272,280 B2 | 3/2016 | Viola et al. |
| 9,410,971 B2 | 8/2016 | Viola et al. |
| 9,915,671 B2 | 3/2018 | Schubert et al. |
| 9,977,039 B2 | 5/2018 | Viola et al. |
| 10,031,144 B2 | 7/2018 | Viola et al. |
| 10,161,944 B2 | 12/2018 | Viola et al. |
| 10,481,168 B2 | 11/2019 | Viola et al. |
| 2002/0013530 A1 | 1/2002 | Cespedes et al. |
| 2002/0040187 A1 | 4/2002 | Alam et al. |
| 2002/0042144 A1 * | 4/2002 | Mann ............ G01N 33/86 |
| | | | 436/69 |
| 2002/0081741 A1 | 6/2002 | Braun et al. |
| 2002/0134176 A1 * | 9/2002 | Bigus ............ B01L 3/0217 |
| | | | 73/864.11 |
| 2003/0013958 A1 | 1/2003 | Govari et al. |
| 2003/0073244 A1 | 4/2003 | Cohen et al. |
| 2003/0105398 A1 | 6/2003 | Vitek |
| 2003/0113929 A1 | 6/2003 | Baugh et al. |
| 2003/0170883 A1 | 9/2003 | Martin et al. |
| 2003/0171676 A1 | 9/2003 | Trahey et al. |
| 2003/0199082 A1 | 10/2003 | Miller |
| 2003/0201878 A1 | 10/2003 | Bai et al. |
| 2003/0204141 A1 | 10/2003 | Nock et al. |
| 2004/0065143 A1 | 4/2004 | Husher |
| 2004/0068184 A1 | 4/2004 | Trahey et al. |
| 2004/0072357 A1 | 4/2004 | Stiene et al. |
| 2004/0076546 A1 | 4/2004 | Bissett |
| 2004/0088317 A1 | 5/2004 | Fabrick et al. |
| 2004/0167403 A1 | 8/2004 | Nightingale et al. |
| 2004/0203163 A1 | 10/2004 | Cohen et al. |
| 2004/0214337 A1 | 10/2004 | Kautzky |
| 2005/0004463 A1 | 1/2005 | Chen et al. |
| 2005/0015001 A1 * | 1/2005 | Lee ............ A61B 8/12 |
| | | | 600/369 |
| 2005/0053305 A1 | 3/2005 | Li et al. |
| 2005/0148899 A1 | 7/2005 | Walker et al. |
| 2005/0164373 A1 | 7/2005 | Oldham et al. |
| 2005/0215901 A1 | 9/2005 | Anderson et al. |
| 2005/0216987 P1 | 9/2005 | Murakami |
| 2005/0233460 A1 * | 10/2005 | Clague ............ G01N 11/14 |
| | | | 436/69 |
| 2007/0038095 A1 | 3/2007 | Greenleaf et al. |
| 2007/0059840 A1 | 3/2007 | Cohen et al. |
| 2007/0078631 A1 | 4/2007 | Ariyoshi et al. |
| 2007/0166195 A1 * | 7/2007 | Padmanabhan ... B01L 3/502715 |
| | | | 422/68.1 |
| 2007/0184508 A1 | 8/2007 | Cohen et al. |

(56) References Cited

U.S. PATENT DOCUMENTS

| | | |
|---|---|---|
| 2007/0237677 A1 | 10/2007 | Kautzky |
| 2007/0259348 A1 | 11/2007 | Phadke et al. |
| 2007/0266778 A1 | 11/2007 | Corey et al. |
| 2007/0276236 A1 | 11/2007 | Jong |
| 2008/0038828 A1 | 2/2008 | Cohen et al. |
| 2008/0194967 A1 | 8/2008 | Sliwa et al. |
| 2008/0200343 A1 | 8/2008 | Clemens |
| 2008/0249408 A1 | 10/2008 | Palmeri et al. |
| 2008/0261261 A1 | 10/2008 | Grimes et al. |
| 2008/0297169 A1 | 12/2008 | Greenquist et al. |
| 2009/0112483 A1 | 4/2009 | Cohen |
| 2009/0130645 A1 | 5/2009 | Schubert et al. |
| 2009/0269837 A1 | 10/2009 | Shevkoplyas et al. |
| 2010/0154520 A1 | 6/2010 | Schubert |
| 2010/0190193 A1 | 7/2010 | Calatzis et al. |
| 2010/0274130 A1 | 10/2010 | Anand et al. |
| 2011/0034805 A1 | 2/2011 | Walker et al. |
| 2011/0151491 A1 | 6/2011 | Dennis et al. |
| 2011/0172661 A1 | 7/2011 | Designer et al. |
| 2011/0252352 A1 | 10/2011 | Viola et al. |
| 2012/0232803 A1 | 9/2012 | Viola et al. |
| 2012/0244392 A1 | 9/2012 | Kleiman |
| 2012/0252127 A1 | 10/2012 | Bansil et al. |
| 2012/0294767 A1 | 11/2012 | Viola et al. |
| 2013/0190584 A1 | 7/2013 | Walker et al. |
| 2018/0275150 A1 | 9/2018 | Viola et al. |

FOREIGN PATENT DOCUMENTS

| | | | |
|---|---|---|---|
| CN | 101035479 | 9/2007 | |
| CN | 103649751 | 3/2017 | |
| DE | 20201402289 | 9/2014 | |
| EP | 1162457 | 12/2001 | |
| EP | 1347058 | 9/2003 | |
| EP | 1901065 | 3/2008 | |
| EP | 2555704 | 2/2013 | |
| EP | 2676143 | 12/2013 | |
| EP | 3001196 | 3/2016 | |
| WO | 0250535 | 6/2002 | |
| WO | 2008093216 | 8/2008 | |
| WO | WO-2009142638 A1 * | 11/2009 | ............... C12Q 1/56 |
| WO | 2009152094 | 12/2009 | |
| WO | 2011035162 | 3/2011 | |
| WO | 2011127436 | 10/2011 | |
| WO | 2012159021 | 2/2012 | |
| WO | 2013105987 | 10/2013 | |
| WO | 2015184433 | 12/2015 | |

OTHER PUBLICATIONS

Viola, et al., "A novel ultrasound-based method to evaluate hemostatic function of whole blood," Clinica Chimica Acta, vol. 411, No. 1-2, pp. 106-113. (Year: 2010).*
Amukele, et al., "Comparison of plasma with whole blood prothrombin time and fibrinogen on the same instrument," American Journal of Clinical Pathology, vol. 133, No. 4, Apr. 2010, pp. 550-556.
Anderson, "Multi-Dimensional Velocity Estimation with Ultrasound Using Spatial Quadrature," IEEE Transactions on Ultrasonics Ferroelectrics & Frequency Control, vol. 45, No. 3, 1998, pp. 852-861.
Anderson, "Preventing Deep Vein Thrombosis and Pulmonary Embolism," Center for Outcomes Research, U Mass Med Center, 1998, 23 pages.
Becker, R., "Cell-based models of coagulation: a paradigm in evolution," Journal of Thrombosis and Thrombolysis, vol. 20, No. 1, Aug. 2005, pp. 65-68.
Bercoff et al., "In vivo breast tumor detection using transient elastography," Ultrasound in Medicine & Biology, vol. 29, No. 10, 2003, pp. 1387-1396.
Bercoff, et al., "Supersonic Shear Imaging: A New Technique for Soft Tissue Elasticity Mapping," IEEE Transactions on Ultrasonics Ferroelectrics & Frequency Control, vol. 51, No. 4, 2004, pp. 396-409.

Bilgen, et al., "Error analysis in acoustic elastography. II. Strain estimation and SNR analysis", Journal of the Acoustical Society of America, vol. 101, 1997, pp. 1147-1154.
Bohs, et al., "A Real Time System for Quantifying and Displaying Two-Dimensional Velocities using Ultrasound," Ultrasound in Medicine & Biology, vol. 19, No. 9, Jul. 1993, pp. 751-761.
Bonnefous, et al., "Time Domain Formulation of Pulse-Doppler Ultrasound and Blood Velocity Estimation by Cross Correlation," Ultrasonic Imaging 8, 1986, pp. 73-85.
Brock, et al., "Assessing Thrombin Generation at the Point of Care," Clinical Chemistry, vol. 55, No. 3, Mar. 2009, pp. 398-399.
Carr, M., "In vitro assessment of platelet function," Transfusion of Medicine Reviews, vol. 11, No. 2, Apr. 1997, pp. 106-115.
Carroll, et al., "Measurement of functional fibrinogen levels using the Thrombelastograph," Journal of Clinical Anesthesia, vol. 20, No. 3, May 2008, pp. 186-190.
Carter, G., "Coherence and time delay estimation," Proc IEEE, vol. 75, No. 2, 1987, pp. 236-255.
Chakroun et al., "The influence of fibrin polymerization and platelet-mediated contractile forces on citrated whole blood thromboelastography profile," Thrombosis and Haemostasis, vol. 95, No. 5, May 2006, pp. 822-828.
Chandler, et al., "Development of a rapid emergency hemorrhage panel," Tranfusion, vol. 50, No. 12, Dec. 2010, pp. 2547-2552.
Chandler, et al., "Estimating the rate of thrombin and fibrin generation in vivo during cardiopulmonary bypass," Blood, vol. 101, No. 11, Jun. 2003, pp. 4355-4362.
Chaturvedi, et al., "Testing the limitations of 2-D companding for strain imaging using phantoms," IEEE Transactions on Ultrasonics Ferroelectrics & Frequency Control, vol. 45, 1998, pp. 1022-1031.
Cohn et al., "An elasticity microscope. Part I: Methods," IEEE Transactions on Ultrasonics Ferroelectrics & Frequency Control, vol. 44, 1997, pp. 1304-1319.
Cohn et al., "An elasticity microscope. Part II: Experimental Results," IEEE Transactions on Ultrasonics Ferroelectrics & Frequency Control, vol. 44, 1997, pp. 1320-1331.
Craft, et al., "A novel modification of the Thrombelastograph assay, isolating platelet function, correlates with optical platelet aggregation," The Journal of Laboratory and Clinical Medicine, vol. 143, No. 5, May 2004, pp. 301-309.
Dahlback, B., "Blood Coagulation," Lancet, vol. 355, No. 9215, May 2000, pp. 1627-1632.
Emelianov et al., "Ultrasound Elasticity Imaging of Deep Venous Thrombosis," Proc. IEEE Ultrasonics Symp., 2000, pp. 1791-1794.
Evans, et al., "Rheometry and associated techniques for blood coagulation studies," Medical Engineering and Physics, vol. 30, No. 6, Jul. 2008, pp. 671-679.
Fatemi et al., "C-Scan Imaging by Radiation Force Stimulated Acoustic Emission Method," Proc. IEEE Ultrasonics Symp., 1996, pp. 1459-1462.
Fatemi, et al., "Application of radiation force in noncontact measurement of the elastic parameters," Ultrasonic Imaging, vol. 21, No. 2, Apr. 1999 pp. 147-154.
Fatemi, et al., "Ultrasound-Stimulated Vibro-Acoustic Spectography," Science Magazine, vol. 280, No. 5360, 1998, pp. 82-85.
Fertner, et al., "Comparison of Various Time Delay Estimation Methods by Comptuer Simulation," IEEE Transactions on Acoustics, Speech, and Signal Processing, vol. 34, No. 5, 1986, pp. 1329-1330.
Flax, et al., "Phase-Aberration Correction Using Signals From Point Reflectors and Diffuse Scatterers: Basic Principles," IEEE Transactions on Ultrasonics Ferroelectrics & Frequency Control, vol. 35, No. 6, Nov. 1988, pp. 758-767.
Gallippi, et al., "Adaptive clutter filtering via blind source," Ultrasonic Imaging, vol. 24, No. 4, 2002, pp. 193-214.
Gallippi, et al., "BSS-based filtering of physiological and ARFI-induced tissue and blood motion," Ultrasound in Medicine and Biology, vol. 29, No. 11, 2003, pp. 1583-1592.
Gallippi, et al., "Complex blind source separation for acoustic radiation force impulse imaging in the peripheral vasculature, in vivo," IEEE Ultrasonics Symposium, vol. 1, 2004, pp. 596-601.
Gauss, et al., "Wavefront Estimation in the Human Breast," presented at SPIE Medical Imaging, vol. 4325, 2001, pp. 172-180.

(56) References Cited

OTHER PUBLICATIONS

Giunta, et al., "Estimation of Global Motion Parameters by Complex Linear Regression," IEEE Transactions on Image Processing, vol. 8, No. 11, 1999, pp. 1652-1657.
Hartley, et al., "Characteristics of Acoustic Streaming Created and Measured by Pulsed Doppler Ultrasound," IEEE Transactions on Ultrasonics, Ferroelectrics, and Frequency Control, vol. 44, No. 6, Nov. 1997, pp. 1278-1285.
Hartley, et al., "Doppler Measurement of Acoustic Streaming," IEEE Ultrasonics Symposium Proceedings, 1995, pp. 1537-1540.
Huang, et al., "Characterization of Blood Properties from Coagulating Blood of Different Hematocrits Using Ultrasonic Backscatter and Attenuation", Japanese Journal of Applied Physics, vol. 45, No. 9A, 2006, pp. 7191-7196.
Huang, et al., "Detection of blood coagulation and clot formation using quantitative ultrasonic parameters," Ultrasound in Medicine and Biology, vol. 31, No. 11, Nov. 2005, pp. 1567-1573.
Jacovitti, et al., "Discrete Time Techniques for Time Delay Estimation," IEEE Transactions on Signal Processing, vol. 41, No. 2, Feb. 1993, pp. 525-533.
Jensen, "A New Method for Estimation of Velocity Vectors," IEEE Transactions on Ultrasonics, Ferroelectrics and Frequency Control, vol. 45, No. 3, 1998, pp. 837-851.
Jensen, Estimation of Blood Velocities Using Ultrasound, 1996, pp. 195-225.
Jensen, et al., "Calculation of pressure fields from arbitrarily shaped, apodized, and excited ultrasound transducers," IEEE Transactions on Ultrasonics, Ferroelectrics, and Frequency Control, vol. 39, 1992, pp. 262-267.
Jolliffe, IT., "Principal Component Analysis," Springer Series in Statistics, 2nd edition, Springer, NY, 2002, pp. 1-8.
Kadi, et al., "On the performance of regression and step-initialized IIR Clutter Filters," IEEE Transactions on Ultrasonics, Ferroelectrics, and Frequency Control, vol. 42, 1995, pp. 827-837.
Kasai, et al., "Real-time Two-Dimensional Blood Flow Imaging Using an Autocorrelation Technique," IEEE Ultrasonics Symposium, vol. 32, No. 3, 1985, pp. 458-464.
Kruse, et al., "A new high resolution color flow system using an eigendecomposition-based adaptive filter for clutter rejection," IEEE Transactions on Ultrasonics, Ferroelectrics, and Frequency Control, vol. 49, No. 10, 2002, pp. 1384-1399.
Ledoux, et al., "Reduction of the clutter component in Doppler ultrasound signals based on singular value decomposition: a simulation study," vol. 19, No. 1, 1997, pp. 1-18.
Lerner, et al., "Sono-elasticity: medical elasticity images derived from ultrasound signals in mechanically vibrated targets," Ultrasound in Medicine & Biology, vol. 16, 1998, pp. 317-327.
Loupas, et al., "An axial Velocity Estimator for Ultrasound Blood flow imaging, by means of a two-dimensional autocorrelation approach," IEEE Transactions on Ultrasonics, Ferroelectrics, and Frequency Control, vol. 42, No. 4, 1995, pp. 672-688.
McAleavey, et al., "Estimates of echo correlation and measurement bias in acoustic radiation force impulse imaging," IEEE Transactions on Ultrasonics Ferroelectrics & Frequency Control, vol. 50, 2003, pp. 631-641.
Nielson, er al., "Effects of coagulation factor deficiency on plasma coagulation kinetics determined via thrombelastography: critical roles of fibrinogen and factors II, VII, X and XII," Acta Anesthesiologica Scandanavia, vol. 49, No. 2, Feb. 2005, pp. 222-231.
Nightingale, et al., "Shear-Wave Generation Using Acoustic Radiation Force: In Vivo and EX Vivo Results," Ultrasound in Medicine & Biology, vol. 29, No. 12, 2003, pp. 1715-1723.
O'Donnell, et al., "Internal Displacement and Strain Imaging using Ultrasonic Speckle Tracking," IEEE Transactions on Ultrasonics, Ferroelectrics and Frequency Control, vol. 41, 1994, pp. 314-325.
Ophir, et al., "Elastography: A Quantitative Method for Imaging the Elasticity of Biological Tissues," Ultrasonic Imaging, vol. 13, No. 2, 1991, pp. 111-134.
Patil, et al., "3D prostate elastography: algorithm, simulations and experiments," Physics in Medicine & Biology, vol. 52, No. 12, 2007, pp. 3643-3663.
Perry, et al., "Point-of-care testing in haemostasis," British Journal of Haematology, vol. 150, No. 5, Sep. 2010, pp. 501-514.
Sarvazyan, et al., "Shear Wave Elasticity Imagining—A New Ultrasonic Technology of Medical Diagnostics," Ultrasound in Medicine and Biology, vol. 24, 1998, pp. 1419-1436.
Shi, Quantitative Investigation of Acoustic Streaming in Blood, J. Acoust. Soc. Am. 111, Feb. 2002, pp. 1110-1121.
Shi, et al., "Color Doppler Detection of Acoustic Streaming in a Hematoma Model," Ultrasound in Medicine and Biology, vol. 27, No. 9, 2001, pp. 1255-1264.
Shi, et al., "Color Doppler imaging of acoustic streaming in blood and clot," IEEE Ultrasonics Symposium, vol. 2, 1999, pp. 1315-1318.
Shi, et al., "Experimental Investigation and Finite Element Simulation of Streaming in Blood in Cylindrical Models," IEEE Ultrasonics Symposium, vol. 2, 2000, pp. 1509-1512.
Shung, et al., "Ultrasonic characterization of blood during coagulation," Journal of Clinical Ultrasound, vol. 12, No. 3, 1984, pp. 147-153.
Skovoroda, et al., "Tissue elasticity reconstruction based on ultrasonic displacement and strain images," IEEE Transactions on Ultrasonics, Ferroelectrics, and Frequency Control, vol. 42, No. 4, 1995, pp. 747-765.
Sugimoto, et al., "Tissue Hardness Measurement Using the Radiation Force of Focused Ultrasound," Proc. IEEE Ultrason. Symp., 1990, pp. 1377-1380.
Sumino, et al., "Measurements of ultrasonic pulse arrival time differences produced by abdominal wall specimens," Journal of the Acoustical Society of America, vol. 90, No. 6, 1991, pp. 2924-2930.
Thuerlemann, et al., "Monitoring thrombin generation by electrochemistry: development of an amperometric biosensor screening test for plasma and whole blood," Clinical Chemistry, vol. 55, No. 3, Mar. 2009, pp. 505-512.
Toner, et al., "Blood-on-a-chip," Annual Review of Biomedical Engineering, vol. 7, 2005, pp. 77-103.
Torr, "The Acoustic Radiation Force," Am. J. Phys., vol. 52, 1984, pp. 402-408.
Trahey, et al., "Synthetic receive aperture imaging with correction for motion and for tissue inhomogeneities. II. Effects of and correction for motion," IEEE Transactions on Ultrasonics, Ferroelectrics, and Frequency Control, vol. 39, No. 4, 1992, pp. 496-501.
Viola, et al., "A Spline Based Algorithm for Continuous Time Delay Estimation Using Sampled Data," IEEE Transactions on Ultrasonics Ferroelectrics & Frequency Control, in press, 2005, pp. 80-93.
Viola, et al., "Analysis of Clot Formation with Acoustic Radiation Force," SPIE Proceedings, vol. 4689, 2002, pp. 235-242 and pp. 1-2.
Viola, et al., "Comparison of Time Delay Estimators in Medical Ultrasound," IEEE Ultrasonics Symposium, vol. 2, 2001, pp. 1485-1488.
Viola, et al., "Efficient and Accurate Spline-Based Time Delay Estimation," IEEE Ultrasonics Symposium, vol. 2, 2004, pp. 870-873.
Viola, et al., "Imaging Viscoelastic Properties of the Vitreous," Ultrasonics Symposium, vol. 2, 2001, pp. 1623-1626.
Viola, et al., "Radiation Force Imaging of Viscoelastic Properties with Reduce Artifacts," IEEE Transactions on Ultrasonics, Ferroelectrics, and Frequency Control, vol. 50, No. 6, 2003, pp. 736-742.
Viola, et al., "Sonorheometry: A new Method for Assessing coagulation potential," IEEE Ultrasonics Symposium, vol. 1, 2007, pp. 1001-1004.
Viola, et al., "Sonorheometry: A Noncontact Method for the Dynamic Assessment of Thrombosis," The Annals of Biomedical Engineering, vol. 32, 2004, pp. 696-705.
Viola, et al., "Ultrasound echo decorrelation due to acoustic radiation force," IEEE Ultrasonics Symposium Proceedings, vol. 2, 2002, pp. 1903-1906.

(56) References Cited

OTHER PUBLICATIONS

Walker, et al., "Application of Acoustic Radiation Force in Ophthalmic Ultrasound," Proc. IEEE Ultrason. Symp., vol. 2, 1997, pp. 1291-1295.
Walker, et al., "Real-Time Imaging of Tissue Vibration Using a Two-Dimensional Speckle Tracking System," IEEE Ultrason. Symp., 1993, pp. 873-877.
Walker, et al., "The Significance of Correlation in Ultrasound Signal Processing," SPIE Proceedings, vol. 4325, 2001, pp. 159-171.
Westbrook, et al., "Protocol based on thromboelastograph (TEG) out-performs physician preference using laboratory coagulation tests to guide blood replacement during and after cardiac surgery: a pilot study," Heart, Lung, and Circulation, vol. 18, No. 4, Aug. 2009, pp. 277-288.
Yu, et al., "Single-Ensemble-Based Eigen-Processing Methods For Color Flow Imaging," IEEE Transactions on Ultrasonics, Ferroelectrics, and Frequency Controls, vol. 55, No. 3, 2008, pp. 573-587.
Beer: Center for Reproductive Immunology & Genetics, "Thrombophilia: Inherited and Acquired," 6 pages, http://repro-med.net/papers/thromb.php.
Bell, et al., "Thrombelastographic evaluation of coagulation in transurethral prostatectomy," British Journal of Urology, vol. 78, No. 5, 1996, pp. 737-741.
Bombeli, et al., "Updates in perioperative coagulation: physiology and management of thromboembolism and haemorrhage," British Journal of Anaesthesia; vol. 93, No. 2, Aug. 2004, pp. 275-287.
Chavez, J., "A novel thromboelastograph tissue factor/kaolin assay of activated clotting times for monitoring heparin anticoagulation during cardiopulmonary bypass," Anesthesia and Analgesia; vol. 99, No. 5 Nov. 2004, pp. 1290-1294.
Curry, et al., "Convention and near-patient tests of coagulation," British Journal of Anaesthesia, vol. 7, No. 2, Apr. 2007, pp. 45-50.
Despotis, et al., "Monitoring of hemostasis in cardiac surgical patients: impact of point-of-care testing on blood loss and transfusion outcomes," Clinical Chemistry, vol. 43, No. 9, Sep. 1997, pp. 1684-1696.
Embree, et al., "Volumetric Blood Flow via Time-Domain Correlation: Experimental Verification," IEEE Transactions on Ultrasonics Ferroelectrics & Frequency Control, vol. 37, No. 2, May 1990, pp. 176-189.
Ferraris, et al., "2011 Update to The Society of Thoracic Surgeons and the Society of Cardiovascular Anesthesiologists Blood Conservation Clinical Practice Guidelines," Annals of Thoracic Surgery, vol. 91, 2011, pp. 944-982.
Freedman, et al., "A Meta-Analysis of Thromboembolic Prophylaxis Following Elective Total Hip Arthroplasty," Journal of Bone and Joint Surgery, vol. 82-A, 2000, pp. 929-938.
Gaetano, G. de, et al., "Effect of Platelets on Clot Structuration, a Thrombelastographic Study," Thrombosis Research, vol. 3, No. 4, pp. 425-435, 1973.
Ganter, et al., "Active, personalized, and balanced coagulation management saves lives in patients with massive bleeding," Anesthesiology, vol. 133, No. 5, Nov. 2010, pp. 1016-1018.
Ganter, et al., "Coagulation monitoring: current techniques and clinical use of viscoelastic point-of-care coagulation devices," Anesthesia and Analgesia, vol. 106, No. 5, May 2008, pp. 1366-1375.
Gauss, et al., "Adaptive Imagining in the Thyroid Using Fundamental and Harmonic Echo Data," presented at IEEE Ultrasonics Symposium, 1999, pp. 1515-1519.
Glidden, Paul F., et al., "Thromboelastograph Assay for Measuring the Mechanical Strength of Fibrin Sealant Clots," Clinical and Applied Thombosis/Hemostasis, vol. 6, No. 4, Oct. 2000, pp. 226-233.
Gottumkkala, Vijaya N., et al., "Assessing Platelet and Fibrinogen Contribution to Clot Strength Using Modified Thromboelastography in Pregnant Women," Anesth Analg, vol. 89, 1999, pp. 1453-1455.
Greilich, Philip E., et al., "A Modified Thromboelastographic Method for Monitoring c7E3 Fab in Heparinized Patients," Anesth Analg, vol. 84, 1997, pp. 31-38.
Greilich, Philip E., et al., "Near-Site Monitoring of the Antiplatelet Drug Abciximad Using the Hemodyne Analyzer and Modified Thrombelastograph," Journal of Cardiothoracic and Vascular Anesthesis, vol. 13, No. 1, Feb. 1999, pp. 58-64.
Gurbel, et al., "Platelet function monitoring in patients with coronary artery disease," Journal of the American College of Cardiology, vol. 50, No. 19, Nov. 2007, pp. 1822-1834.
Harris, et al., "Evaluation of recurrent thrombosis and hypercoagulability," American Family Physician, vol. 56, No. 6, Oct. 1997, pp. 1591-1596, pp. 1601-1602.
Hett, et al., "Sonoclot Analysis," British Journal of Anaesthesia, vol. 75, No. 6, Dec. 1995, pp. 771-776.
Hirsh, et al., "How we diagnose and treat deep vein thrombosis," Blood, vol. 99, 2002, pp. 3102-3110.
Hirsh, et al., "Management of deep vein thrombosis and pulmonary embolism. A statement for healthcare professionals," Council on Thrombosis (in consultation with the Council on Cardiovascular Radiology), American Heart Association, vol. 93, 1996, 55 pages.
Hoffman, et al., "A cell-based model of hemostasis," Thrombosis and Haemostasis, vol. 85, No. 6, Jun. 2001, pp. 958-965.
Ickx, Brigitte, "Point-of-Care Monitoring of Haemostasis in the OR and the ICU," European Society of Anaesthesiologists. Jun. 5, 2004, pp. 79-83.
International Search Report and Written Opinion of the International Searching Authority, received in corresponding application PCT/US2010/049342, dated Nov. 16, 2010.
International Search Report and Written Opinion of the International Searching Authority, received in corresponding application PCT/US2011/031832, dated Dec. 15, 2011.
Ivandic, et al., "Determination of clopidogrel resistance by whole blood platelet aggregometry and inhibitors of the P2Y12 receptor," Clinical Chemistry, vol. 52, No. 3, Mar. 2006, pp. 383-388.
Katori, et al., "The effects of platelet count on clot retraction and tissue plasminogen activator-induced fibrinolysis on thrombelastography," Anesthesia and Analgesia, vol. 100, No. 6, Jun. 2005, pp. 1781-1785.
Keresztes, et al., "The PFA-100: analysis and interpretation of a platelet function measurement," The Journal of Cardiovascular Nursing, vol. 20, No. 6, 2005, pp. 405-407.
Kettner, S.C., et al., "Use of abciximab-Modified Thrombelatography in Patients Undergoing Cardiac Surgery," Anesth Analg, vol. 89, 1999, pp. 580-584.
Khurana, Sandeep, et al., "Monitoring Platelet Glycoprotein IIb/IIa-fibrin Interaction with Tissue Factor-Activated Thromboelastography," J Lab Clin Med, vol. 130, No. 4, 1997, pp. 401-411.
Khurana, Sandeep, et al., "Thromboelastography Can Rapidly Bioassay Fibrinogen," Anesthesiology, vol. 85, No. 3A, Sep. 1996, p. A457.
Koepke, J., "Point-of-Care Coagulation Testing," Laboratory Medicine, vol. 31, No. 6, Jun. 2000, pp. 343-346.
Lubinski, et al., "Adaptive strain estimation using retrospective processing medical US elasticity imaging," IEEE Transactions on Ultrasonics Ferroelectrics & Frequency Control, vol. 46, 1999, pp. 97-107.
Mahla, et al., "Thromboelastography for monitoring prolonged hypercoagulability after major abdominal surgery," Anesthesia and Analgesia, vol. 92, No. 3, Mar. 2001, pp. 572-577.
Malinin, et al., "Validation of a VerifyNow-P2Y12 cartridge for monitoring platelet inhibition with clopidogrel," Methods and Findings in Experimental and Clinical Pharmacology, vol. 28, No. 5, Jun. 2006, pp. 315-322.
Mauldin, et al., "Robust Principal Component Analysis and Clustering Methods for Automated Classification of Tissue Response to ARFI Excitation," Ultrasound in Medicine & Biology, vol. 34, No. 2, 2008, pp. 309-325.
Mauldin, F.W., Jr., et al., "Adaptive Force Sonorheometry for Assessment of Whole Blood Coagulation," Clin. Chim. Acta., May 2, 2010, vol. 411, No. 9-10, pp. 638-644.
International Search Report and Written Opinion, dated Jan. 2, 2013, received from the Korean Intellectual Property Office in connection with related application No. PCT/US2012/038553.

(56) References Cited

OTHER PUBLICATIONS

Ng, et al., "A Comparative Evaluation of Several Algorithms for Phase Aberration Correction," IEEE Transactions on Ultrasonics Ferroelectrics & Frequency Control, vol. 41, No. 5, Sep. 1994, pp. 631-643.

Nightingale, et al., "Acoustic Radiation Force Impulse Imaging: In Vivo Demonstration of Clinical Feasibility," Ultrasound in Medicine & Biology, vol. 28, 2002, pp. 227-235.

Nightingale, et al., "Acoustic remote palpation: initial in vivo results," presented at IEEE Ultrasonics Symposium, 2000, pp. 1553-1558.

Oberhardt, et al., "Dry reagent technology for rapid, convenient measurements of blood coagulation and fibrinolysis," Clinical Chemistry, vol. 37, No. 4, Apr. 1991, pp. 520-526.

O'Donnell, et al., "Role of the Thrombelastograph as an adjunctive test in thrombophilia screening," Blood Coagulation and Fibrinolysis, vol. 15, No. 3, Apr. 2004, pp. 207-211.

Packham, M., "Role of platelets in thrombosis and hemostasis," Canadian Journal of Physiology and Pharmacology, vol. 72, No. 3, Mar. 1994, pp. 278-284.

Palmeri, et al., "Ultrasonic tracking of acoustic radiation force-induced displacements in homogeneous media," IEEE Transactions on Ultrasonics, Ferroelectrics, and Frequency Control, vol. 53, No. 7, 2006, pp. 1300-1313.

Parsons, et al., "Age Deterniniation of Experimental Venous Thrombi by Ultrasonic Tissue Characterization," Journal of Vascular Surgery, vol. 17, 1993, 470-478.

Pivalizza, et al., "Perioperative thromboelastography and sonoclot analysis in morbidly obese patients," Canadian Journal of Anaesthesia, vol. 44, No. 9, Sep. 1997, pp. 942-945.

Rao, G., "Need for a point-of-care assay for monitoring antiplatelet and antithrombotic therapies," Stroke, vol. 40, No. 6, Jun. 2009, pp. 2271-2272.

Riou, et al., "Fast adaptive eigenvalue decomposition: a maximum likelihood approach," IEEE International Conference on Acoustics, Speech, and Signal Processing, vol. 5, 1997, pp. 3565-3568.

Rubin, et al., "Clinical application of sonographic elasticity imaging for aging of deep venous thrombosis: preliminary findings," Journal of Ultrasound in Medicine, vol. 22, 2003, pp. 443-448.

Sakharov, et al., "Acceleration of Fibrinolysis by High-Frequency Ultrasound: The Contribution of Acoustic Streaming and Temperature Rise," Thrombosis Research, vol. 100, No. 4, 2000, pp. 333-340.

Srinivasan, et al., "Elastographic imaging using staggered strain estimates," Ultrasonic Imaging, vol. 24, 2002, pp. 229-245.

Strobach, P., "Low-rank adaptive filters," IEEE Trans Signal Process, vol. 44, No. 12, 1996, pp. 2932-2947.

Traverso C, Arcelus JI, Gomez E, Luna D, Lopez-Cantarero M, Garcia JM. "Prospective assessment of the risk of deep vein thrombosis in elective abdominal surgery. Predictive role of [Thrombelastograph® analysis]." Thromb Haemorrh Disorders. 1993:71:9-15.

Vig, et al., "Thromboelastography: a reliable test?," Blood Coagulation and Fibrinolysis, vol. 12, No. 7, Oct. 2001, 555-561.

Viola, et al., "A Comparison between spline-based and phase-domain time-delay estimators," IEEE Transactions on Ultrasonics, Ferroelectrics, and Frequency Control, vol. 53, No. 3, 2006, pp. 515-517.

Viola, et al., "A comparison of the performance of time-delay estimators in medical ultrasound," IEEE Transactions on Ultrasonics Ferroelectrics & Frequency Control., vol. 50, 2003, pp. 392-401.

Walker, et al., "A Fundamental Limit on Delay Estimation Using Partially Correlated Speckle Signals," IEEE Transactions on Ultrasonics, Ferroelectrics and Frequency Control, vol. 42, 1995, pp. 301-308.

Walker, et al., "A Fundamental Limit on the Accuracy of Speckle Signal Alignment," IEEE Ultrasonics Symposium Proceedings, vol. 3, 1994, pp. 1787-1791.

Walker, et al., "A Method of Imagining Viscoelastic Parameters with Acoustic Radiation Force," Physics in Medicine and Biology, vol. 45, No. 6, 2000, pp. 1437-1447.

Whitten, et al., "Thromboelastography: past, present, and future," Anesthesiology, vol. 92, No. 5, May 2000, pp. 1223-1225.

Azar et al., "Abciximab in Primary Coronary Angioplasty for Acute Myocardial Infarction Improves Short- and Medium-Term Outcomes", J. Am. Coll. Cardiol., Dec. 1998; 32(7):1996-2002. PubMed P.M.I.D.: 9857884.

Blättlr W, Straub PW, Peyer A. Effect of in vivo produced fibrinogen-fibrin intermediates on viscosity of human blood. Thrombosis research. 1974;4(6):787-801.

Born, G.V., "Aggregation of Blood Platelets by Adenosine Diphosphate and its Reversal". Nature, Jun. 9, 1962; 194:927-9. PubMed P.M.I.D.: 13871375.

Callé et al., "Evaluation of the Sensitivity of an in vitro High Frequency Ultrasound Device to Monitor the Coagulation Process: Study of the Effects of Heparin Treatment in a Murine Model". Ultrasound Med. Biol., Feb. 2010; 36(2):295-305. PubMed P.M.I.D.: 20045589.

Coiffic et al., "Inhibition of Platelet Aggregation by Abciximab but not by Aspirin can be Detected by a New Point-of-Care Test, the Hemostatus". Thromb. Res., Jul. 15, 1999, 95(2):83-91. PubMed P.M.I.D.: 10418797.

Communication pursuant to Article 94(3) EPC dated Apr. 3, 2018 in European Application No. 12865280.7.

Communication Pursuant to Article 94(3) EPC issued for European Application No. 12865280.7, dated Mar. 18, 2019, 7 pages.

Communication Pursuant to Article 94(3) EPC, issue for European Application No. 12865280.7, dated Oct. 8, 2018, 17 pages.

Communication pursuant to Rule 114(2) EPC issued in European Patent Application No. 12865280.7, dated Dec. 13, 2016, 5 pages.

Communication pursuant to Rule 94(3)) EPC issued in European Patent Application No. 12865280.7, dated Jul. 3, 2017, 3 pages.

Examination Report issued in European Application No. 12865280.7, dated Mar. 7, 2017, 3 pages.

Extended Search Report issued in European Patent Application No. 12865280, dated Oct. 24, 2016, 5 pages.

Conduct of Proceeding for Inter Partes Review of U.S. Pat. No. 9,272,280 B2 dated Apr. 26, 2018, 3 pages.

Conduct of Proceeding For Inter Partes Review of U.S. Pat. No. 9,410,971 dated Apr. 26, 2018, 3 pages.

Conduct of Proceeding For Inter Partes Review of U.S. Pat. No. 9,410,971 dated May 24, 2018, 5 pages.

Cuisset T, Frere C, Poyet R, et al. Clopidogrel response: Head-to-head comparison of different platelet assays to identify clopidogrel non-responder patients after coronary stenting. Archives of Cardiovascular Diseases. 2010;103(1):39-45.

Decision Denying Petitioner's Request for Rehearing for Inter Partes Review of U.S. Pat. No. 9,410,971, entered Nov. 3, 2017, 7 pages.

Decision to Institute for Inter Partes Review of U.S. Pat. No. 9,915,671, dated Oct. 5, 2018, 27 pages.

Declaration of Dr. Scott Diamond, Ph.D., dated Dec. 1, 2017.

Declaration of Frank M. Laduca, Ph.D, dated Feb. 21, 2019, 117 pages.

Declaration of Frank M. Laduca, Ph.D, FAHA, dated Apr. 24, 2019, 130 pages.

Declaration of John Avila for Inter Partes Review of U.S. Pat. No. 9,915,671, dated Jan. 4, 2019, 38 pages.

Declaration of Patrick D. Mize, Ph.D., dated Nov. 30, 2017.

Declaration of Scott Diamond for Inter Partes Review of U.S. Pat. No. 9,915,671 dated Apr. 20, 2018, 200 pages.

Declaration of U.S. Pat. No. 9,272,280, 67 pages.

Declaration of U.S. Pat. No. 9,410,971,124 pages.

Delhaye et al., Temperature corrected thromboelastometry in hypothermic trauma patients: 6AP24. European Journal of Anaesthesiology, May/Jun. 2008, 25:84.

Dorn-Beineke et al., "Evaluation of the Automated Coagulation Analyzer Sysmex CA-7000". Thromb. Res., 2005; 116(2):171-9 PubMed P.M.I.D.:15907533.

(56) References Cited

OTHER PUBLICATIONS

Douning et al., "Temperature Corrected Thrombelastography in Hypothermic Patients". Anesthesia & Analgesia, Oct. 1995; 81(3):608-11.
Eikelboom et al., "Monitoring Unfractionated Heparin with the aPTT: Time for a Fresh Look". Thromb. Haemost. Nov. 2006; 96(5):547-52. Review. PubMed P.M.I.D.: 17080209.
Examination Report issued for Australian Application No. 2017248548, dated Jul. 9, 2018.
Examination Report issued in Australian Application No. 2012364908, dated Jun. 27, 2017, 5 pages.
Extended European Search Report issued in European Patent Application No. 11766842.6, dated Oct. 21, 2015, 10 pages.
Third party observation filed in European Patent Application No. 11766842.6, dated Mar. 6, 2016, 10 pages.
Faulds, D. et al., "Abciximab (c7E3 Fab). A review of its pharmacology and therapeutic potential in ischaemic heart disease; Drugs 583-98 (1994)" PubMed P.M.I.D.: 7528131 ("Faulds 1994").
Final Written Decision For Inter Partes Review of U.S. Pat. No. 9,272,280, dated Feb. 13, 2019, 25 pages.
Final Written Decision For Inter Partes Review of U.S. Pat. No. 9,410,9710, dated Feb. 13, 2019, 55 pages.
Flanders et al., "Evaluation and Performance Characteristics of the STA-R Coagulation Analyzer". Clin Chem., Sep. 2002; 48(9):1622-4. PubMed P.M.I.D.: 12194955.
Fricke, W., Kouides, P., Kessler, C., Schmaier, A.H., Krijanovski, Y., Jagadeesen, K., Joist, J., A multicenter clinical evaluation of the Clot Signature Analyzer. J. Thromb. Hasemostasis. 2004; 2:763-8.
Fundamentals of biomechanics Equiolobrium, Motion, and Deformation. 2nd Edition. Eds. Nihat Özkaya and Margareta Nordin. (Springer Science+Business Media, Inc., New York, NY). Chapter 9 "Mechanical Properties of Biological Tissues." pp. 196-218. 1999.
Fundamentals of biomechanics Equiolobrium, Motion, and Deformation. 3rd Edition. Eds. Nihat Özkaya and Margareta Nordin. (Springer Science+Business Media, Inc., new York, NY). Chapter 15"Mechanical Properties of Biological Tissues." pp. 221-236. 2012.
Ganter et al., "Kaolin-Based Activated Coagulation Time Measured by Sonoclot in Patients Undergoing Cardiopulmonary Bypass." J. Cardiothorac. Vasc. Anesth, Aug. 2007; 21(4):524-8. PubMed P.M.I.D.: 17678778.
Gorlinger et al., "Recommendations for using the ROTEM® in the management of perioperative bleeding in Cardiac Surgery" Recommendations from the ROTEM® Expert Meeting Working Group, Munich 2007, 10 pages.
Görlinger, K., et al., "Perioperative Coagulation Management and Control of Platelet Transfusion by Point-of-Care Platelet Function Analysis," Transfus Med Hemother 34:396-411 (2007).
Gosselin et al., "Monitoring Oral Anticoagulant Therapy with Point-of-Care Devices: Correlations and Caveats". Clin. Chem., Sep. 1997; 43(9):1785-6. PubMed P.M.I.D.: 9299978.
Hanecke, P and Klouche, M, Thrombelastography Today: Practicability and Analytical Power, Transfusion Medicine and Hemotherapy. 34. 421-428 (2007) ("Hanecke").
Hardisty R. M. et al, "Fibrinogen as a Co-factor in the Reaction of Platelets with Kaolin," May 7, 1966, Nature Publishing Group, Edition 210, vol. 644 (http://www.nature.com/nature/journal/v210/n5036/abs/210644a0.html).
Harrison, P. Platelet Function Analysis. Blood Rev. Mar. 2005; 19(2):111-23. Review. PubMed P.M.I.D.: 15603914.
Hemostasis and Thrombosis, Basic Principles and Clinical Practice. 3rd Edition. Eds. Colman R.W., Hirsh J., Marder V.J., Salzman E.W. (J.B. Lippincott Company, Philadelphia). Chapter 1 "Overview of Hemostasis" by R.W. Colman, V.J. Marder, E.W. Salzman, J. Hirsh. pp. 3-18. 1994.
Hirsh et al., "Oral anticoagulants. Mechanism of Action, Clinical Effectiveness, and Optimal Therapeutic Range". Chest. Oct. 1992; 102(4 Suppl.):3125-3265. Review. PubMed P.M.I.D.: 1345417.
Instrument Engineers' Handbook. Fourth Edition. Ed. Bela G. Liptak (CRC Press). Process Measurement and Analysis vol. 1, Chapter 8 Analytical Instrumentation. 8.53 Rheometers, 1628-1636, 2003.
*Instrumentation Laboratory Co. v. HemoSonics LLP*, IPR2017-00852, Paper No. 47 (PTAB Feb. 13, 2019) ("852 FWD").
*Instrumentation Laboratory Co. v. HemoSonics LLP*, IPR2017-00855, Paper No. 55 (PTAB Feb. 13, 2019) ("'971 FWD").
International Preliminary Report on Patentability and Written Opinion, dated Oct. 8, 2013, in connection with International Application No. PCT/US2012/025270.
International Preliminary Report on Patentability and Written Opinion, dated Aug. 27, 2013, in connection with International Application No. PCT/US2012/025278.
International Preliminary Report on Patentability and Written Opinion, dated Nov. 19, 2013, in connection with International Application No. PCT/US2012/038553.
International Preliminary Report on Patentability and Written Opinion, dated Oct. 9, 2012, in connection with International Application No. PCT/US2011/031832.
International Preliminary Report on Patentability and Written Opinion, dated Mar. 20, 2012, in connection with International Application No. PCT/US2010/049342.
International Search Report, dated Aug. 20, 2013, in connection with International Application No. PCT/US2012/025278.
International Search Report, dated Sep. 30, 2013, in connection with International Application No. PCT/US2012/025270.
International Search Report and Written Opinion, dated Oct. 31, 2018, in connection with International Application No. PCT/US2018/028630, 18 pages.
Janmey PA, Erdile L, Bale MD, Ferry JD. Kinetics of fibrin oligomer formation observed by electron microscopy. Biochemistry. 1983;22(18):4336-40.
Janus TJ, Lewis SD, Lorand L, Shafer JA. Promotion of thrombin-catalyzed activation of factor XIII by fibrinogen. Biochemistry. 1983;22(26):6269-72.
Jobes et al., "Increased Accuracy and Precision of Heparin and Protamine Dosing Reduces Blood Loss and Transfusion in Patients Undergoing Primary Cardiac Operations". J. Thorac. Cardiovasc. Surg. Jul. 1995; 110(1):36-45. PubMed P.M.I.D.: 7609566.
Kereiakes et al., "Time Course, Magnitude, and Consistency of Platelet Inhibition by Abciximab, Tirofiban, or Eptifibatide in Patients with Unstable Angina Pectoris Undergoing Percutaneous Coronary Intervention". Am. J. Cardiol., Aug. 15, 1995; 84(4):391-5. PubMed P.M.I.D.: 10468074.
Koster et al., "Evaluation of Post-Cardiopulmonary Bypass Coagulation Disorders by Differential Diagnosis with a Multichannel Modified Thromboelastogram: A Pilot Investigation". J. Extra. Corpor. Technol., Sep. 2001; 33(3):153-8. PubMed P.M.I.D.: 11680728.
S. Kozek-Langenecker, Intensive Care Medicine, Annual Update 2007, Monitoring of Hemostasis in Emergency Medicine, pp. 847-860, Springer New York.
Kuntamukkula MS, McIntire L V, Moake JL, Peterson DM, Thompson WJ. Rheological studies of the contractile force within platelet-fibrin clots: effects of prostaglandin E1, dibutyryl-cAMP and dibutyryl-cGMP. Thrombosis research. 1978;13(6):957-69.
Lang et al., "Possibilities and limitations of thromboeleastometry/thromboelastography," Downloaded from www.haemostaseologie-online.com on Mar. 6, 2018 | IP: 24.163.60.123.
Lang et al., "Multi-center investigation on reference ranges from ROTEM thromboelasatometry", Blood coagul. Fibrinol 16:4, 2005, pp. 301-310.
Lang, T., et al., "Different effects of abciximab and cytochalasin D on clot strength in thrombelastography," Journal of Thrombosis and Haemostasis, 2: 147-153 (2004), PubMed P.M.I.D.: 14717978.
Li et al., "The Xylum Clot Signature Analyzer: A Dynamic Flow System that Simulates Vascular Injury". Thromb. Res., Dec. 15, 1998; 92(6 Suppl. 2):567-77. PubMed P.M.I.D.: 9886913.
Libgot, R., et al., "High frequency ultrasound characterization of the blood clotting process: intra- and inter-individual variations," 2005 IEEE Ultrasonics Symposium, IEEE, vol. 4, 2005, pp. 2259-2262.

(56) References Cited

OTHER PUBLICATIONS

Machado et al., "Evaluation of an Ultrasonic Method Applied to the Measurement of Blood Coagulation Time". Physiol. Meas., May 1997; 18(2):129-43. PubMed P.M.I.D.: 9183807.
Mauldin, W. et al. Adaptive force sonorheometry for assessment of whole blood coagulation, Clin Chim Acta. May 2, 2010;411(9-10):638-44. doi:10.1016/j.cca.2010.01.018.https://linkinghub.elsevier.com/retrieve/pii/S0009-8981(10)00031-8.
Moake J Overview of Hemostasis. Merck Manuals 2016 http://www.merckmanuals.com/professional/hematology-and-oncology/hemostasis/overview-of-hemostasis.
Motovska et al., "Benefits and Risks of Clopidogrel Use in Patients with Coronary Artery Disease: Evidence from Randomized Studies and Registries". Clin. Ther., 2008; 30 Pt. 2:2191-202. J. Clinthera., 2008.12.001. Review. PubMed P.M.I.D.: 19281914.
Mueller et al., "Utility of the PFA-100 Instrument and the Novel Multiplate Analyzer for the Assessment of Aspirin and Clopidogrel Effects on Platelet Function in Patients with Cardiovascular Disease". Clin. Appl. Thromb. Hemost., Dec. 2009; 15(6):652-9. PubMed P.M.I.D.: 18805846.
Multiplate® Analyzer Product Guide.
Nam et al., "Evaluation of the Roche CoaguChek XS Handheld Coagulation Analyzer in a Cardiac Outpatient Clinic". Ann. Clin. Lab. Sci., 2008 Winter; 38(1):37-40. PubMed P.M.I.D.: 18316780.
Nielson V, A Comparison of the Thrombelastograph and ROTEM, Blood Coagulation and Fibrinolysis 18:3, 247-252, 2007.
Niewiarowski S, Stewart GJ, Nath N, Sha AT, Lieberman GE. ADP, thrombin, and Bothrops atrox thrombinlike enzyme in platelet-dependent fibrin retraction. The American journal of physiology. 1975;229(3):737-45.
Office Action issued for Canadian Application No. 2,823,729, dated Mar. 9, 2018.
Office Action issued for Canadian Application No. 2,823,729, dated Nov. 14, 2018, 4 pages.
Office Action issued for Canadian Application No. 2,823,729, dated Aug. 14, 2019, 12 pages.
Office Action issued for Chinese Application No. 2017101635956, dated Jul. 17, 2018. English Translation.
Office Action issued for Chinese Application No. 2017101635956, dated Apr. 26, 2019.
Office Action issued for U.S. Appl. No. 15/904,984, dated Jul. 12, 2018.
Office Action issued for U.S. Appl. No. 15/904,984, dated Dec. 4, 2018.
Notice of Allowance issued for U.S. Appl. No. 15/904,984, dated Aug. 21, 2019.
Pallister CJ, Watson MS (2010). Haematology. Scion Publishing. pp. 336-347. ISBN 1-904842-39-9.
Patent Examination Report issued in Australian Application No. 2012364908, dated Jul. 23, 2016, 4 pages.
Patent Owner's Preliminary Response for Inter Partes Review for U.S. Pat. No. 9,915,671 dated Jul. 20, 2018, 14 pages.
Patent Owner's Preliminary Response to Petition Requesting Inter Partes Review of U.S. Pat. No. 9,410,971, dated Feb. 14, 2018, 33 pages.
Patent Owner's Response For Inter Partes Review of U.S. Pat. No. 9,915,671, dated Jan. 4, 2019, 37 pages.
Patent Owner's Response to the Decision to Institute Inter Partes Review of U.S. Pat. No. 9,410,971, entered Dec. 1, 2017, 59 pages.
Patent Owner's Response to the Decision to Institute Inter Partes Review of U.S. Pat. No. 9,272,280, dated Dec. 1, 2017, 39 pages.
Peeters et al., "Ultrasonic Measurements of Coagulation and Fibrinolysis". J. Clin. Pathol., May 1964; 17:320-3. PubMed P.M.I.D.: 14159472; PubMed Central P.M.C.I.D.: PMC480759.
Petition for Inter Partes Review for U.S. Pat. No. 9,915,671 dated Apr. 20, 2018, 76 pages.
Petition For Inter Partes Review Of U.S. Pat. No. 9,272,280 B2, 28 Pages.
Petition For Inter Partes Review Of U.S. Pat. No. 9,410,971 B2, 51 Pages.
Petition For Inter Partes Review Of U.S. Pat. No. 9,410,971, dated Nov. 30, 2017, 74 pages.
Petition for Post-Grant Review of U.S. Pat. No. 9,977,039, dated Feb. 21, 2019, 95 pages.
Petition for Post-Grant Review of U.S. Pat. No. 10,031,144, dated Apr. 24, 2019, 104 pages.
Petitioner's Supplemental Reply For Inter Partes Review of U.S. Pat. No. 9,272,280 B2 dated May 18, 2018, 10 pages.
Petitioner's Reply to Patent Owner's Response of U.S. Pat. No. 9,272,280 dated Mar. 1, 2018, 17 pages.
Petitioner's Reply to Patent Owner's Response of U.S. Pat. No. 9,410,971 dated Mar. 1, 2018, 25 pages.
Plotkin, et al., The Journal of Trauma: Injury, Infection, and Critical Care. 2008.
Price et al., "Prognostic Significance of Post-Clopidogrel Platelet Reactivity Assessed by a Point-ofCcare Assay on Thrombotic Events after Drug-Eluting Stent Implantation". Eur. Heart J., Apr. 2008; 29(8):992-1000. PubMed P.M.I.D.: 18263931.
Prisco et al. "Point-of-Care Testing of Hemostasis in Cardiac Surgery". Thromb. J. May 6, 2003; 1(1):1, 10 pages. PubMed P.M.I.D.: 12904262; PubMed Central P.M.I.D.: PMC166118.
Rahe-Meyer, N. et al., Multicentric comparison of single portion reagents and liquid reagents for thromboelastometry. Blood Coagul Fibrinolysis Apr. 2009;20(3):218-22. PubMed P.M.I.D.: 19657320.
Rugeri et al."Diagnosis of early coagulation abnormalities in trauma patients by rotation thrombelastography", Journal of Thrombosis and Haemostasis, 5, 2007, pp. 289-295.
Rumbaut et al. "Platelet-Vessel Wall Interactions in Hemostasis and Thrombosis" (2010), San Rafael (CA): Morgan & Claypool Life Sciences, 5 pages.
Ruzicka, K., et al. Evaluation of Bedside Prothrombin Time and Activated Partial Thromboplastin Time Measurement by Coagulation Analyzer COAGUCHECK PLUS in Various Clinical Settings. Throm. Res., 87(5)1997 pp. 431-440. See also, Hillman, R., 1988 U.S. Pat. No. 4,756,884. Capillary Fill Device.
Scharbert et al., "Evaluation of the Platelet Mapping Assay on Rotational Thromboelastometry ROTEM". Platelets. Mar. 2009;20(2):125-30. PubMed P.M.I.D. 19235055.
Schmitt, C., et al., "Characterization of blood clot viscoelasticity by dynamic ultrasound elastography and modeling of the rheological behavior," Journal of Biomechanics, vol. 44, No. 4, 2011, pp. 622-629.
Schochl et al., "Use of rotation thromboelastometry (ROTEM) to achieve successful treatment of polytrauma with fibrinogen concentrate and prothrombin complex concentrate", Anaesthesia, 2010, 65, pp. 199-203.
Shih, C-C, et al., "In Vitro Assessments of Viscoelastic Properties of Fibrin Clot by Using Acoustic Radiation Force on a Solid Sphere," International Ultrasonics Symposium Proceedings, IEEE, 2010, pp. 479-482.
Shore-Lesseron., Evidence Based Coagulation Monitors: Heparin Monitoring, Thromboelastography, and Platelet Function. Sem. Cardiothoracic Vasc. Anesthesia., Mar. 2005; 9(1):42-52.
Spiel, A. O. et al.,"Validation of rotation thrombelastography in a model of systemic activation of fibrinolysis and coagulation in humans", Journal of Thrombosis and Haemostasis, 2006; 4: 411-416.
Stony Brook Portable Field Viscometer (For a quick 'Pass' or 'Fail' decision).
Table of Prior Art Devices.
Taborski et al., "Analytical Performance of the New Coagulation Monitoring System INRatio for the Determination of INR Compared with the Coagulation Monitor Coaguchek S and an Established Laboratory Method" J. Thromb.Thrombolysis. Oct. 2004; 18(2):103-7. PubMed P.M.I.D.: 15789176.
The 510(k) Substantial Equivalence Determination Decision Summary for ROTEM delta, FDA clearance No. K083842 (the"Decision Summary for ROTEM delta").
Theusinger, O.M., Nürnberg, J., Asmis, L.M., Seifert, B., Spahn, D.R., Rotation thromboelastometry (ROTEM) stability and reproducibility over time. Eur. J. Cardiothorac. Surg. 2010; 37:677-83.
Third party observation filed in U.S. Appl. No. 15/202,059, dated Nov. 30, 2016, 40 pages.

(56) References Cited

OTHER PUBLICATIONS

Thurston GB. Viscoelasticity of Human Blood. Biophysical Journal. 1972; 12:1205-1217.
Tomauiolo, M., Brass, L.F., Stalker, T.J., Regulation of Platelet Activation and Coagulation and Its Role in Vascular Injury and Arterial Thrombosis. Interv. Cardiol. Clin. Jan. 2017; 6(1):1-12.
Trial Board Order For Inter Partes Review Of U.S. Pat. No. 9,272,280 B2, 13 pages.
Trial Board Order For Inter Partes Review of U.S. Pat. No. 9,410,971 B2, 27 pages.
Trial Paper For Inter Partes Review of U.S. Pat. No. 9,272,280 B2 dated Jul. 11, 2018, 10 pages.
Trial Paper For Inter Partes Review of U.S. Pat. No. 9,410,971 dated Jul. 11, 2018, 10 pages.
Trial Paper For Inter Partes Review of U.S. Pat. No. 9,410,971 dated Aug. 28, 2018, 3 pages.
Trial Paper For Inter Partes Review of U.S. Pat. No. 9,410,971 dated Oct. 2, 2017, 11 pages.
Trial Paper For Inter Partes Review of U.S. Pat. No. 9,410,971 dated Dec. 1, 2017, 4 pages.
Tripodi et al., "International Sensitivity Index Calibration of the Near-Patient Testing Prothrombin Time Monitor, ProTime". Am. J. Clin. Pathol., Feb. 2003;119(2):241-5. PubMed P.M.I.D.: 12579994.
User Manual (2007) for TEG 5000 Thrombelastograph Hemostasis System with TEG Analytical Software (TAS) Version 4.2.3 including an addendum (2008) for TEG Analytical Software (TAS) Version 4.3 (the "TEG 5000 User Manual").
VerifyNow® Product Guide.
Versteeg et al., "New Fundamentals in Hemostasis", Physiol. Rev. Jan. 2013; 93(1):327-58. Review. PubMed P.M.I.D.: 23303912.
Viola et al., "A Novel Ultrasound-Based Method to Evaluate hemostatic Funtion of Whole Blood", Clin Chim Acta. Jan. 2010; 411(1-2): 106-113., Published online Oct. 25, 2009, PubMed Central P.M.C.I.D. PMC2791922.
Voleišis, A. et al., "Ultrasonic method for the whole blood coagulation analysis," Ultrasonics, vol. 40, May 2002, pp. 101-107.
Webster, Medical Instrumentation: Application and Design, New York: John Wiley & Sons, 1998, 6 pages.
Weisel JW. The mechanical properties of fibrin for basic scientists and clinicians. Biophysical Chemistry. 2004;112(2-3):267-276.
Weiss HJ, Aledort LM, Kochwa S., The effect of salicylates on the hemostatic properties of platelets in man. J Clin Invest. Sep. 1968;47(9):2169-80.
Wolberg AS. Plasma and cellular contributions to fibrin network formation, structure and stability. Haemophilia. May 2010 16:7-12.
Wolff et al., "Aspirin for the Primary Prevention of Cardiovascular Events: an Update of the Evidence for the U.S. Preventive Services Task Force". Ann. Intern. Med., Mar. 17, 2009; 150(6):405-10. Review. PubMed P.M.I.D.: 19293073.
Summons to attend oral proceeding pursuant to Rule 115(1) EPC European Patent Application No. 12865280.7, dated Dec. 5, 2019.
Ganter et al., "Coagulation Monitoring: Current Techniques and Clinical Use of Viscoelastic Point-of-Care Coagulation Devices," International Anesthesia Research Society, vol. 106, No. 5, May 2008, pp. 1366-1375.
Office Action issued for Chinese Application No. 2017101635956, dated Sep. 27, 2019.
Notice of Grant issued for Chinese Application No. 2017101635956, dated Jan. 13, 2020.
Kozek-Langenecker S. Monitoring of Hemostasis in Emergency Medicine in Intensive Care, Annual Update 2007 Ed: Vincent JL.
The 510(k) Summary for ROTEM delta, FDA clearance No. K083842 ("the 510(k) Summary for ROTEM delta").
Patent Owner's Notice of Appeal Inter Partes Review Case No. IPR2018-00950 U.S. Pat. No. 9,915,671B2, dated Feb. 4, 2020, 68 pages.
Office Action issued for Canadian Application No. 2,823,729, dated Apr. 6, 2020.
Wilson, D, et al. "Changes in Coagulability as Measured by Thrombelastography Following Surgery for Proximal Femoral Fracture." Injury, vol. 32, No. 10, 2001, pp. 765-770., doi:10.1016/s0020-1383(01)00139-5. (Year 2001).
Patent Examination Report No. 1 for Australian Application No. 2017201112 dated Apr. 5, 2018, 2 pages. ep.
Office Action issued for Canadian Application No. 2,826,770 dated Feb. 1, 2019, 4 pages.
Communication pursuant to Article 94(3) EPC dated Nov. 18, 2019, for European Application No. 12865373.0, 7 pages.
Office Action issued for U.S. Appl. No. 15/641,731, dated Apr. 20, 2020.
Office Action issued for U.S. Appl. No. 15/641,731, dated Sep. 27, 2019.

* cited by examiner

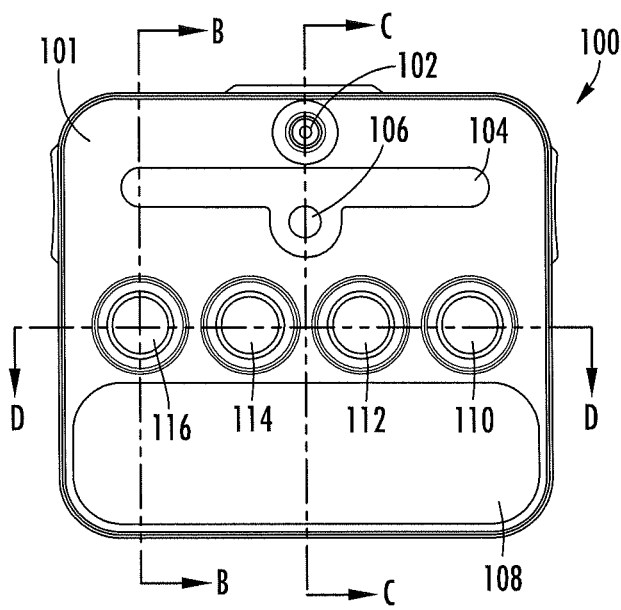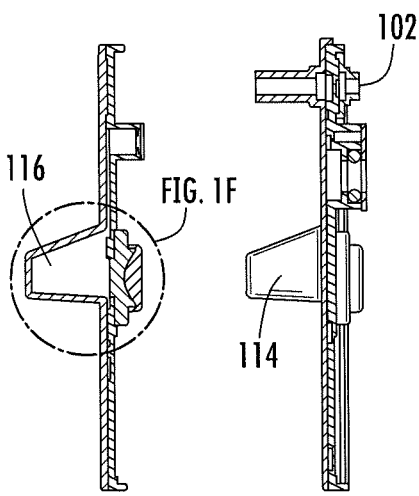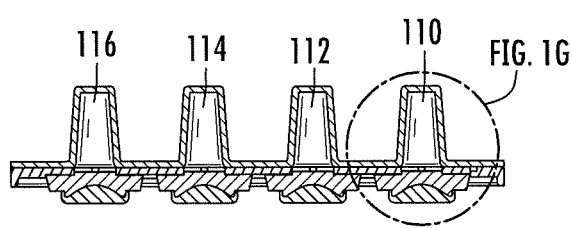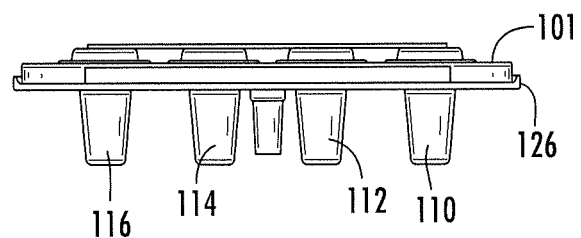

HEMOSTASIS ANALYZER

CROSS REFERENCE TO RELATED APPLICATIONS

This application is a continuation application of U.S. application Ser. No. 13/475,347, filed on May 18, 2012, which claims the benefit of U.S. Provisional Application No. 61/488,046, filed on May 19, 2011, each of which is incorporated by reference herein in its entirety.

TECHNICAL FIELD

The present application relates to devices, systems and methods for using a portable unit to evaluate hemostasis in a subject by analysis of a test sample from the subject to determine one or more indices of hemostasis.

BACKGROUND

Hemostasis, the physiological control of bleeding, is a complex process incorporating the vasculature, platelets, coagulation factors (FI-FXIII), fibrinolytic proteins, and coagulation inhibitors. Disruption of hemostasis plays a central role in the onset of myocardial infarction, stroke, pulmonary embolism, deep vein thrombosis and excessive bleeding. Consequently, in vitro diagnostics (IVD) are critically needed to quantify hemostatic dysfunction and direct appropriate treatment. This need is particularly acute during cardiac surgeries requiring cardiopulmonary bypass (CPB), where post-surgical bleeding is a common complication requiring transfusion of blood products. Furthermore, a need exists for a portable hemostasis analyzer for personal and remote use outside a primary medical or surgical setting.

Existing IVDs include endpoint biochemical assays, platelet aggregation assays, and clot viscoelastic measurement systems. Endpoint biochemical assays such as the prothrombin time (PT) and the partial thromboplastin time (PTT) are widely used to assess coagulation. However, these tests measure only a part of the hemostatic process and operate under non-physiological conditions incorporating only the function of plasma. As a result of these limitations, complications such as postoperative bleeding often occur despite normal perioperative PT and PTT measurements.

Activated clotting time (ACT) is an endpoint assay that is most often applied in support of CPB. This assay applies strong initiation of the surface activation (intrinsic) pathway to quantify heparinization. Limitations of the ACT include its disregard for platelet function, lysis, and coagulation kinetics along with the use of large aliquots of whole blood (WB) (generally 2 mL) and moving mechanical parts. For these reasons, the ACT is used for rapid assessment of heparinization and associated protamine reversal with limited utility for additional applications.

Platelets play a crucial role in the progression of coagulation and quelling arterial bleeding. Furthermore, the modern cell-based theory of hemostasis recognizes that platelets play a modulating role in coagulation. Platelet function is monitored clinically via both central lab assays and point of care (POC) tests, which use anticoagulated WB. Both approaches are limited in that they use platelet aggregation as a proxy for overall platelet function. Furthermore, disabling coagulation, these methods neglect the interaction between platelets and the coagulation cascade.

Techniques that monitor the viscoelastic properties of WB, such as thromboelastography (TEG) and rotational thromboelastometer (ROTEM), circumvent many of the limitations of endpoint biochemical assays and platelet aggregation assays by measuring the combined effects of all components of hemostasis. TEG has been shown to diagnose hyperfibrinolysis in bleeding patients, indicate transfusion requirements better than standard biochemical assays, and reduce transfusion requirements during CPB when used with transfusion algorithms. While these tests offer valuable clinical information, the devices are typically complex to operate and difficult to interpret. Moreover, the TEG applies relatively large shear strains, which transgress the non-linear viscoelastic regime, thereby disrupting clot formation. For these reasons, the TEG sees very limited utility as a POC test.

Furthermore, methods such as TEG and ROTEM, measure the contribution of all the components of hemostasis in whole blood. The existing mechanical methods, however, utilize complex and expensive mechanical transducers, resulting in instruments that are large, bulky and difficult to operate. These bench-top systems typically weigh well over 10 pounds and are utilized in central laboratory settings. Further, the large mechanical strains (in the range of 8% to 16%) applied to the blood samples have been shown to interfere with clot formation and limit sensitivity and speed of the measurements.

Platelet tests are typically performed in central laboratories using platelet rich plasma, even though whole blood, portable devices have recently emerged, such as the Accumetrics VerifyNow. Limitations include the necessity to perform the measurements with anticoagulated blood, which does not represent actual physiology, and the long turn-around-times to obtain results from the central lab. Therefore, the available portable and compact devices can only assess a single sub-system of hemostasis (i.e., either the function of the coagulation factors or that of platelets). The systems that do provide complete characterization of hemostasis utilize complicated and bulky sensors with moving mechanical parts such that miniaturization is not possible.

SUMMARY

Provided are devices, systems and methods for evaluation of hemostasis with a portable unit.

For example, one implementation includes a portable system for determining a plurality of hemostatic parameters. The system includes a blood sample receptacle, an analyzer and a housing. The blood sample receptacle is configured to hold at least one blood sample. The analyzer is configured to determine at least two hemostatic parameters of the at least one blood sample. The housing is configured to operably couple the blood sample receptacle and the analyzer. The housing is portable and may, for example, have a thickness of 17.5 cm or smaller.

The hemostatic parameters may be determined by measuring changes in viscoelastic properties of the blood over time.

The thickness of the housing may be a minimum outer dimension of the housing and be 2.65 cm or smaller.

The system may further include a pumping mechanism configured to fill the blood sample receptacle. For example, the pumping mechanism may include a micro-pump that is contained within the housing. Also the micro-pump may include a piezo-actuated component and a two-stage diaphragm. Or, the pumping mechanism may include a manually operated pump with a plurality of check valves.

Also, the system may include a temperature mechanism configured to control a temperature of the blood sample. The temperature mechanism may include a heater or a temperature sensor.

Another implementation may include a consumable for holding at least two blood samples. The consumable includes at least two test chambers. Each of the test chambers is configured to hold one of the blood samples and yield a differential hemostatic parameter. The consumable is suited for handheld or compact use by having a maximum test chamber thickness of 11 mm or less.

The consumable may also include chemical reagents for assessing specific hemostatic parameters. For example, the chamber may hold lyophilized reagent. The chamber may be a region of the consumable configured to hold the lyophilized reagents therein.

The consumable may also include an integrated lens and coupling. The lens and coupling may have a total thickness of 8 mm or less. Also, the maximum thickness of the consumable through the lens, coupling and test chamber may be 19 mm or less.

The consumable may include a thermally conductive polymer or a foil having thermal conductive properties. Also, the consumable may be a die cast component, such as an aluminum component.

A heating element may be included in the consumable. The heating element is configured to generate heat for the test chambers and blood samples.

Also, the consumable may include a temperature control device for controlling temperature of the blood samples. For example, the temperature control device may be a Peltier device.

Another implementation includes a portable system having a consumable receptacle, a processor and a display, wherein the system is 10 pounds or less.

The systems may be configured to determine hemostatic indexes including one or more of a coagulation factor function, a fibrinogen concentration, a fibrinogen function, a platelet function and a fibrinolysis function.

The system may be further configured to correct for environmental vibrations.

Another implementation includes a system for determining at least one hemostatic parameter. The system includes a blood sample receptacle, an analyzer and a housing. The blood sample receptacle is configured to hold at least one blood sample and eliminate an interface between the blood sample and a gas.

These and other features and advantages of the present invention will become more readily apparent to those skilled in the art upon consideration of the following detailed description and accompanying drawings, which describe both the preferred and alternative embodiments of the present invention.

BRIEF DESCRIPTION OF THE DRAWINGS

FIGS. 1A-G are schematic illustrations of an example cartridge for evaluating hemostasis.

DETAILED DESCRIPTION

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

As used in the specification, and in the appended claims, the singular forms "a," "an," "the," include plural referents unless the context clearly dictates otherwise.

The term "comprising" and variations thereof as used herein are used synonymously with the term "including" and variations thereof and are open, non-limiting terms.

As used throughout, by a "subject" is meant an individual. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex.

Figure 1F:
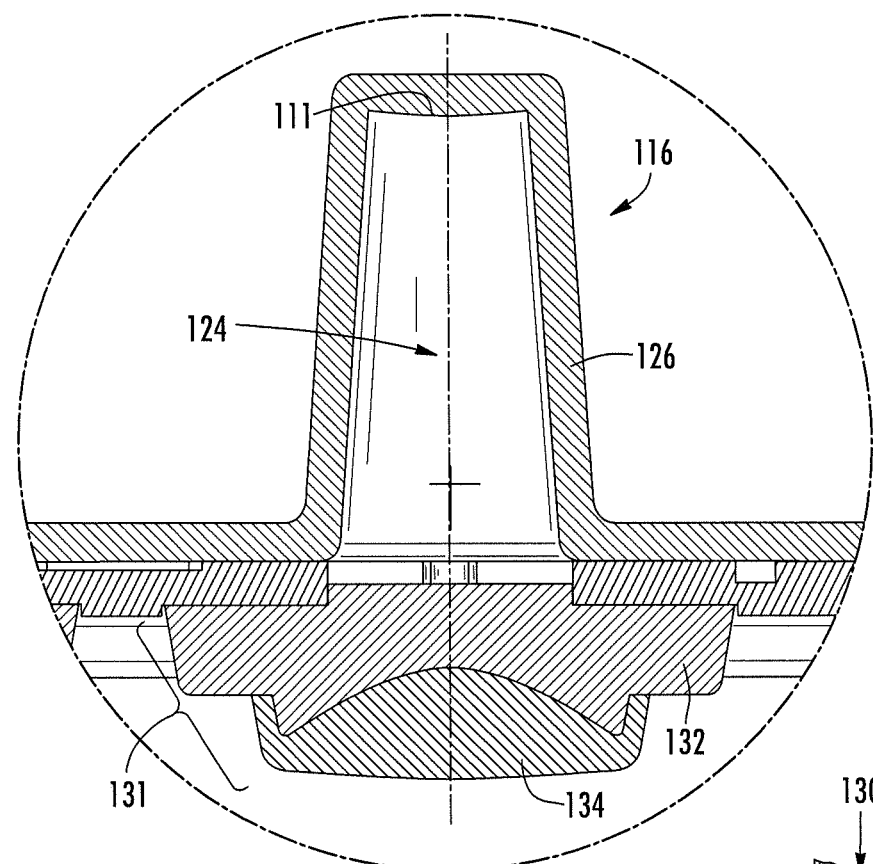

FIGS. 1A-G illustrate an example cartridge 100 for use in evaluation of hemostasis in a subject. The cartridge 100 includes a front surface 101 and a rear surface 126. FIG. 1A shows a front view of the cartridge 100 and the corresponding front surface 101. The cartridge includes an inlet 102, also referred to herein as an inlet port or entry port, such as a nipple, through which a biological sample from the subject can be introduced into the cartridge. Optionally, a blood sample from the subject is introduced into the cartridge at the inlet 102. Another biological sample that may be introduced for analysis is plasma. The inlet 102 is in fluid communication with a channel 202, which is shown in FIG. 2, and which directs the biological sample to other portions of the cartridge as described herein.

The cartridge further includes a port 106 for applying a vacuum to the cartridge. When a vacuum is applied at the port 106, the biological fluid introduced at the inlet 102 into the channel 202 is propelled along the channel 202 towards the port 106.

Figure 2:
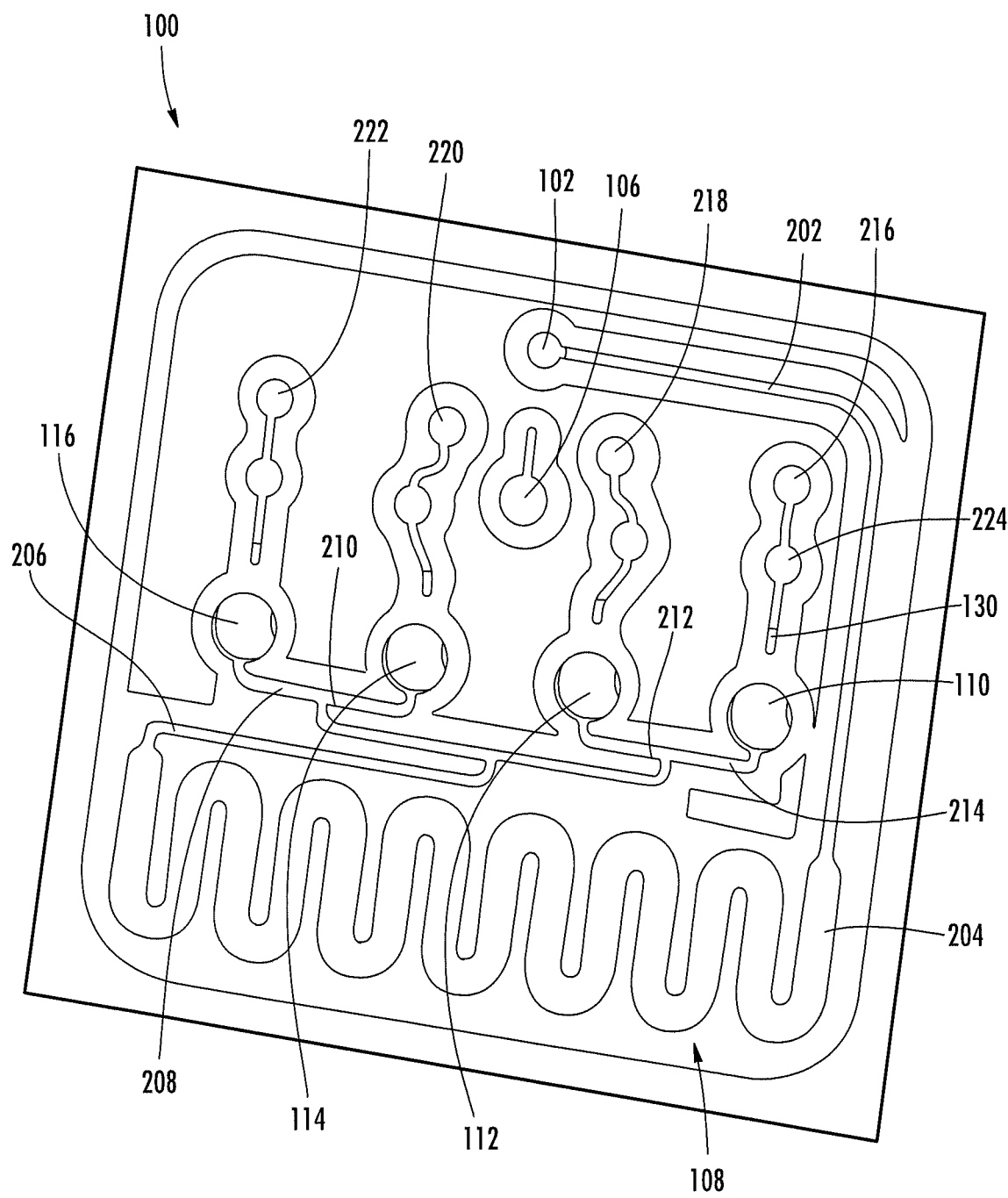
FIG. 2 is a schematic illustration of biological fluid pathways of the example cartridge of FIGS. 1A-G.

As shown in FIG. 2, in moving between the inlet 102 and the port 106, the biological fluid, or a portion thereof, moves along the channel 202, into the channel 204, the channel 206, and along the channels 208, 210, 212 and 214. Each of channels 208, 210, 212 and 214 are in fluid communication with a test chamber, also referred to herein, for example, as a chamber, well, or test well, or the like. For example, as illustrated in FIG. 2, channel 208 is in fluid communication with a test chamber 116, channel 210 is in fluid communication with a test chamber 114, channel 212 is in fluid communication with a test chamber 112, and channel 214 is in fluid communication with a test chamber 110.

Referring again to FIG. 1, each test chamber comprises an open space 124 defined by a portion of the rear surface 126. FIG. 1B shows a cross-sectional illustration through test chamber 116 taken across the line B-B of FIG. 1A. FIG. 1C shows a cross-sectional illustration taken across the line C-C of FIG. 1A. FIG. 1F shows an expanded view of the circled portion of FIG. 1B. Moreover, FIG. 1D shows a cross-sectional illustration across the line D-D of FIG. 1A, which illustrates the open space of each of the four test chambers.

Each test chamber is configured to accept a quantity of the biological fluid into the open space. In reference to test chamber 116, illustrated in detail in FIG. 1F, a portion of the biological fluid introduced at the inlet 102 moves through the channels 202, 204 and 214 and into the open space 124 of the test chamber 116.

The biological fluid can also exit each respective test chamber and continue along an exit channel 130 towards the port 106. Thus, fluid introduced at the inlet 102 flows under vacuum through the device channels and into the test chambers. From each test chamber (110, 112, 114, 116), the biological fluid continues to flow along exit channels towards the vacuum.

Proximate the port 106 each exit channel may direct the flowing biological fluid into a hydrophobic filter at location 222, 220, 218 and 216, respectively. The filters or filter prevents movement of the biological fluid out of the cartridge 100 at the port 106. Because the volume of the channels and the test chamber are fixed, the vacuum can pull the biological fluid into the cartridge until the channels and each test chamber is filled with the biological fluid.

Figure 3:
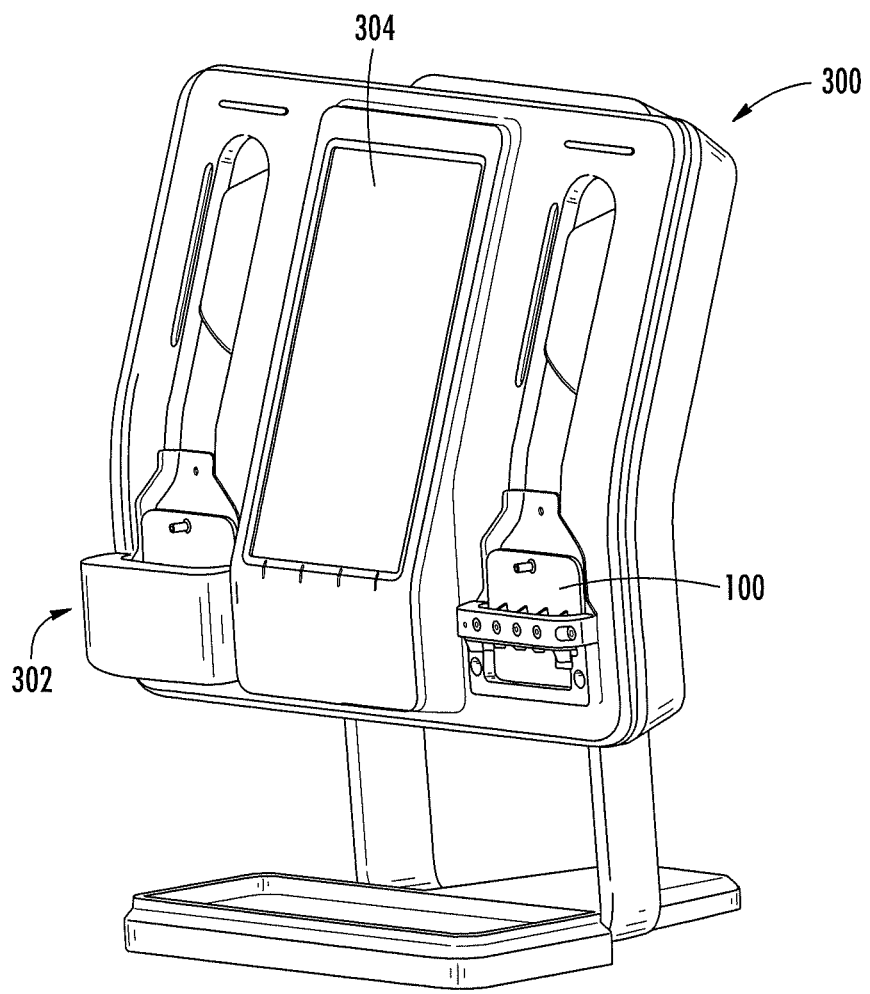
FIG. 3 is a schematic illustration of an example processing system for use with the example cartridge of FIGS. 1A-G.

Pressure can be controlled within the cartridge 100 to, for example, manage flow rate within the consumable 100 and to mitigate reliability issues related to possible user misuse. To measure the properties of a target biological sample, such as a blood sample, a user of the hemostasis system optionally attaches a blood filled syringe to the cartridge 100 unit. There exists the possibility that the user of the hemostasis system 300 (see FIG. 3) could attempt to inject the contents of the applied syringe into the cartridge 100 manually, instead of allowing the device to automatically aspirate the sample. This action may lead to measurement or system error. A pressure management device in the consumable flow path is used to prevent this user action.

Inadequate mixing of the biological sample with the reagents described herein may result in variation of hemostasis measurements. Rapidly aspirating the blood sample is optionally used to provide increased mixing of the reagents with the biological sample, such as a blood sample. This is optionally achieved by creating a pressure differential between the cartridge and the aspirating mechanism of the hemostasis system.

In the portable hemostasis analyzer, a filling mechanism with compact dimensions should be used. For example, a micro-pump, such as the Bartels Mikrotechnik two stage-diaphragm, piezo-actuated micro-pump system, may be used. The portable hemostasis analyzer may optionally include a manually-operated pump system with check valves. Manual operation has the advantage of obviating the need for the weight and space occupied by additional power supply capacity.

Figure 9A:
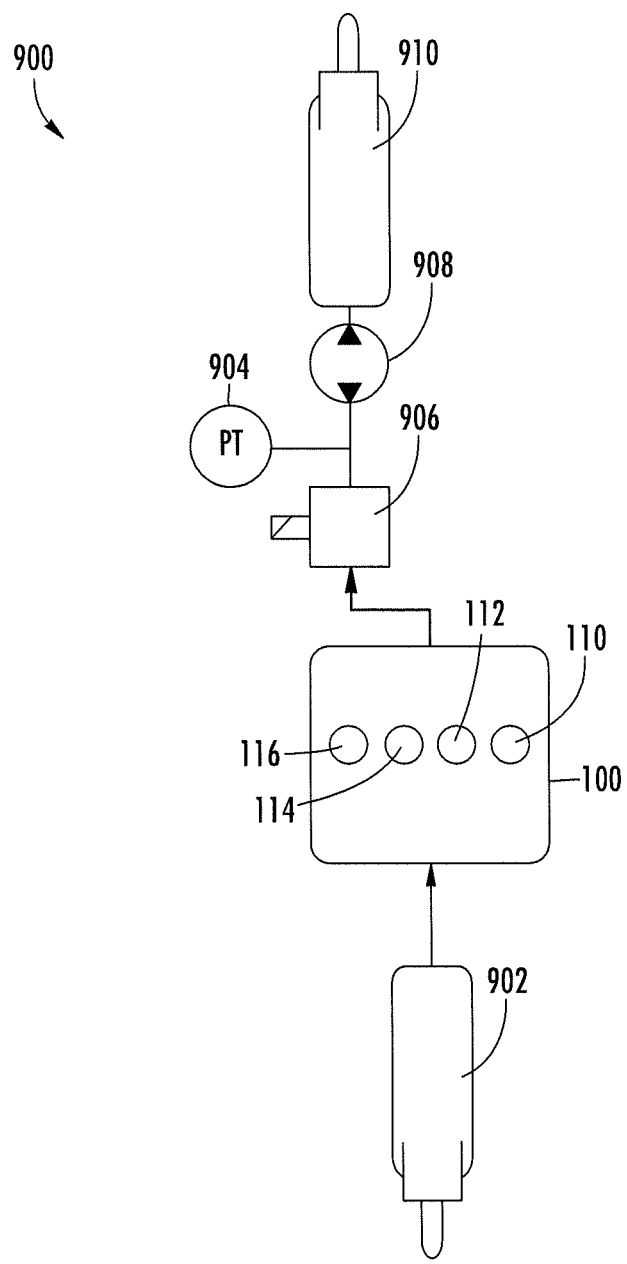
FIGS. 9A-C are schematic illustrations of portions of a system for evaluating hemostasis including pressure control mechanisms.
Figure 9B:
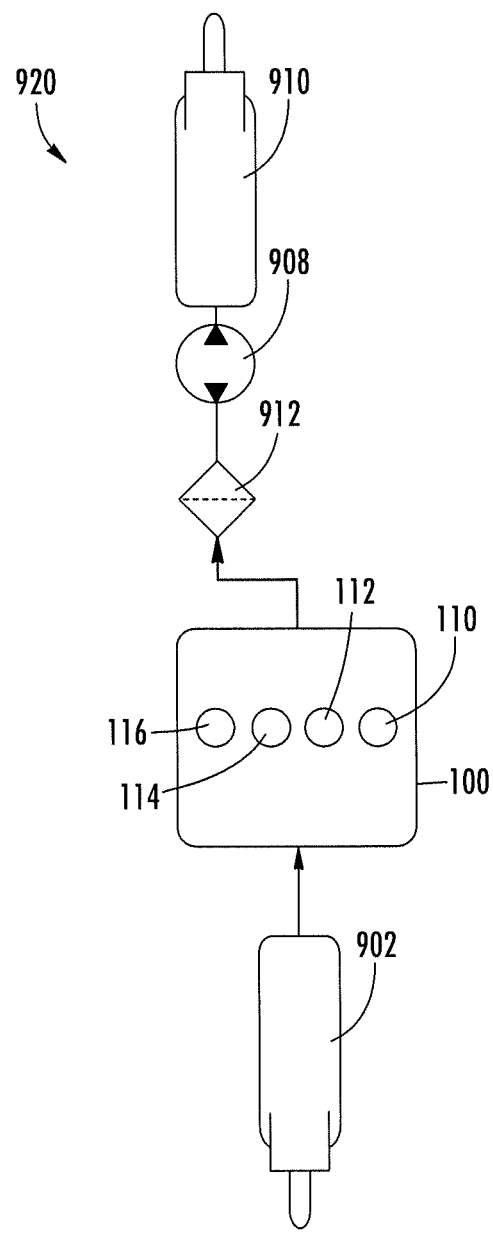
Figure 9C:
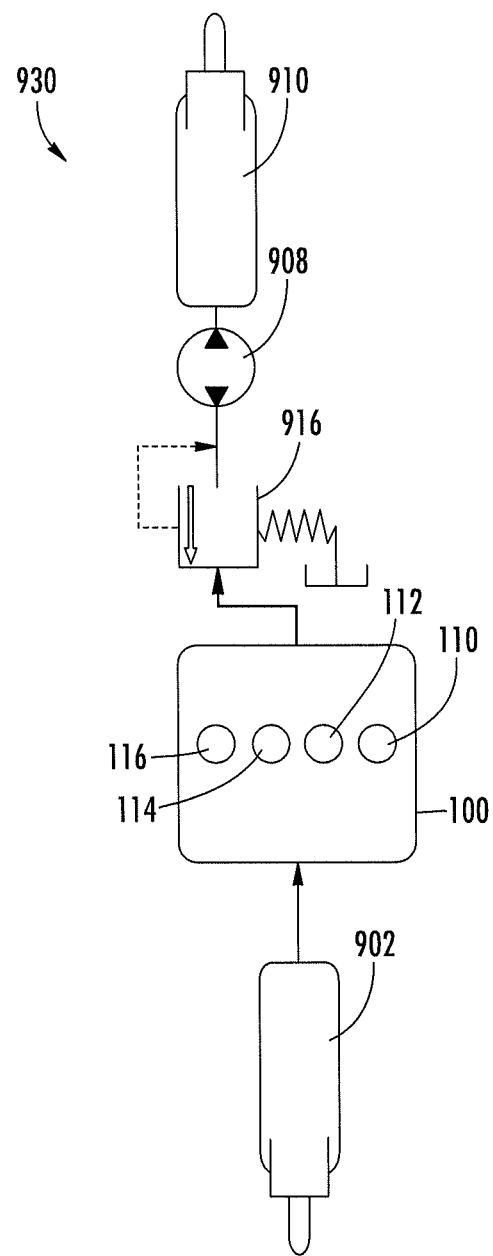

In this regard, FIGS. 9A-C illustrate three example configurations that can be used to control the pressure differential between the cartridge and the aspirating mechanism and can therefore be used to achieve desired levels of mixing and reduce user errors.

FIG. 9A schematically illustrates an example system 900 for controlling pressure in a cartridge 100. The cartridge includes four test chambers (110, 112, 114 and 116). Each test chamber optionally includes a reagent and operation of the system causes a biological sample to enter one or more test chamber. The example system 900 includes a two way pump 908 which operates to aspirate a biological sample, such as a blood sample. For example, a blood sample can be aspirated into the cartridge from a sample container 902. The pump 908 is in fluid communication with the cartridge 100 and therefore activation of the pump can be used to move the biological sample through the cartridge 100. A pressure transducer 904 is in communication with the pump that measures the gauge pressure drawn by the pump 908. A solenoid actuated valve 906 operates to block flow downstream of the pump allowing gauge pressure to build. The solenoid may be selectively actuated to rapidly expose the pressure gradient to the cartridge. The sample is allowed to progress through the cartridge and is optionally collected in a sample container 910.

FIG. 9B schematically illustrates another example system 920 for controlling pressure in a cartridge 100. The cartridge includes four test chambers (110, 112, 114 and 116). Each test chamber optionally includes a reagent and operation of the system causes a biological sample to enter one or more test chamber. The example system 920 includes a two way pump 908 which operates to aspirate a biological sample, such as a blood sample. For example, a blood sample can be aspirated into the cartridge from a sample container 902. The pump 908 is in fluid communication with the cartridge 100 and therefore activation of the pump can be used to move the biological sample through the cartridge 100. A pressure activated membrane 912 is positioned either upstream or downstream of the cartridge 100 from the pump 908. The membrane 912 is configured to rupture at a predetermined cartridge gauge pressure thereby controlling the pressure at which the sample is drawn through the cartridge. The sample is allowed to progress through the cartridge and is optionally collected in a sample container 910.

FIG. 9C schematically illustrates another example system 930 for controlling pressure in a cartridge 100. The cartridge includes four test chambers (110, 112, 114 and 116). Each test chamber optionally includes a reagent and operation of the system causes a biological sample to enter one or more test chamber. The example system 930 includes a two way pump 908 which operates to aspirate a biological sample, such as a blood sample. For example, a blood sample can be aspirated into the cartridge from a sample container 902. The pump 908 is in fluid communication with the cartridge 100 and therefore activation of the pump can be used to move the biological sample through the cartridge 100. A closed loop actuated valve 916 contains an internal pressure control mechanism and is used to block flow downstream from the pump allowing gauge pressure to build until a valve pressure setpoint. Once gauge pressure setpoint is reached the valve 916 deploys thereby exposing the cartridge to a desired pressure gradient. The sample is allowed to progress through the cartridge and is optionally collected in a sample container 910.

Figure 8A:
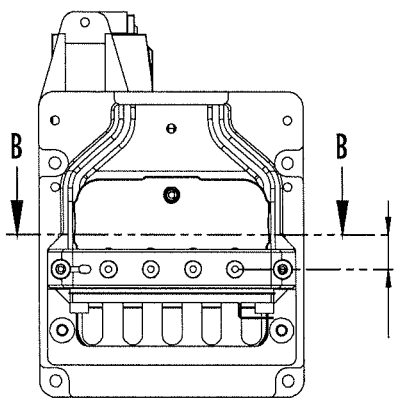
FIGS. 8A-D are schematic illustrations of an example cartridge for evaluating hemostasis.
Figure 8B:
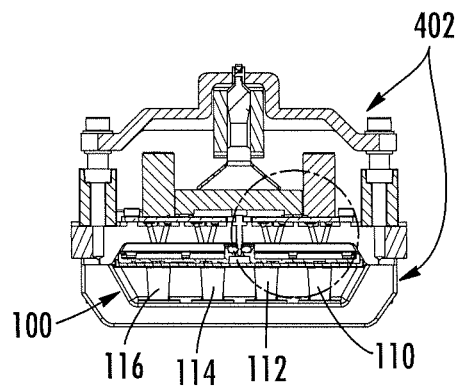
Figure 8C:
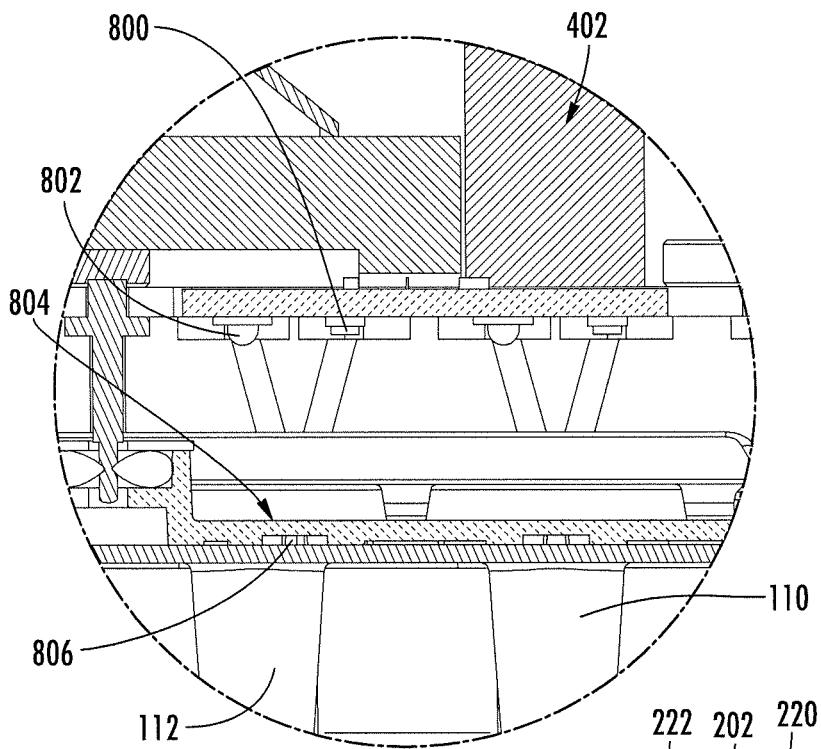
Figure 8D:
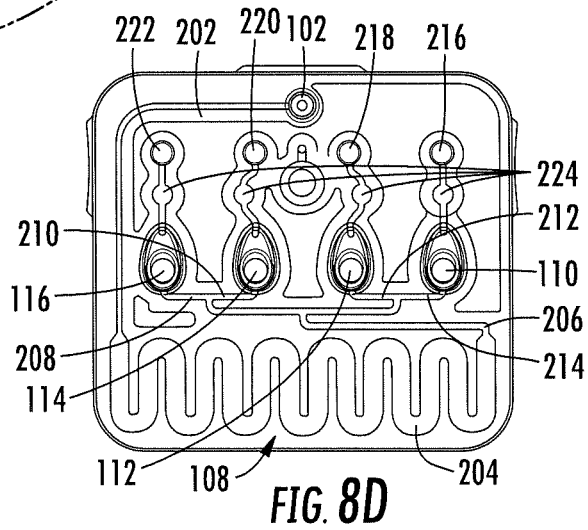

The level of sample in each chamber can also be monitored. For example, as shown in FIGS. 8A-8D, the level of fluid in each chamber can be monitored optically. FIG. 8A is a schematic illustration of an example consumable cartridge placed in an example hemostasis evaluation system. FIG. 8B is a schematic illustration of a cross section taken across line B-B of FIG. 8A. FIG. 8C is an expanded schematic illustration of the circled portion of FIG. 8B. FIG. 8D is a schematic illustration of an example consumable cartridge.

Whether a desired level has been reached in a given chamber can be indicated by a LED or other visual indicator. Employing a single light beam from an LED emitter 802 reflecting off the chamber at a blood detection target reservoir 224, which is then detected by a detector 800 can be optionally used to optically monitor chamber fluid level.

For example, blood entering a test chamber reduces reflection of light originating from an emitter 802 located alongside the detector 800, and pointed at the test chamber. A dual beam approach can be used whereby two sources of different wavelengths were reflected off the test chamber. Blood has a deep red color that can be differentiated by comparing the red wavelength reflection to that of another color.

The difference in intensity of the reflected red light alone is sufficient to determine when blood has entered a chamber. The red light intensity reflected from the test chamber containing blood was about one-half that of the well containing air, and about two-thirds of that from the well containing water.

To control the temperature of the biological sample entering the test chambers, the cartridge 100 can comprise a heat exchanger in communication with the channel 204. The heat exchanger can be used to maintain, elevate or lower the temperature of the biological fluid before analysis in each test chamber. Optionally, the temperature of biological fluid for analysis in each test chamber is the same such that common portion of the channel system, as shown in FIG. 2, is subject to temperature manipulation by the heat exchanger. Optionally, in non-pictured embodiments, the temperature of biological fluid entering each test chamber can be separately controlled.

For example, to heat the biological fluid, it can be passed through the channel 204 through a polystyrene labyrinth held against a copper block. Preferably at least one surface of the polystyrene labyrinth is replaced by a metal foil or a thermally conductive polymer to enhance thermal conduction and thereby enable more rapid heating. The copper block can be thin (for example under 2 mm) and sized just larger than the labyrinth to minimize its thermal mass and enable rapid temperature adjustment. Alternatively the copper block can be large so that the heating process is largely passive, with the thermal mass of the block being substantially greater than that of the blood. A thermistor can be embedded in the block so that a control circuit could maintain a steady set temperature in the block. A heater is used that optionally comprises two Watlow® (St. Louis, Mo.) serpentine foil heating elements bonded to a flexible kapton plastic substrate, and the interface between the block and the heater can be a thin layer of silicone heatsink compound. Alternatively the system might use a Peltier device which can dynamically either heat or cool the sample. An off the shelf Peltier controller, such as the Maxim MAX1978 integrated controller can be employed.

Various flow rates, for example, up to and including 5.99 mL/min or 6.0 mL/min can be used, and power input to the heater can be varied optionally between 8 and 16 Watts. Blood or other biological fluid can be heated in the cartridge from ambient temperature (approximately 20° C.) to 37° C. at a nominal flow rate of 6 mL/min, which is fast enough to fill the cartridge in 20 seconds. The surface area of the labyrinth used was less than 8 cm$^2$. By replacing one surface of the labyrinth with a more conductive material (foil or thermally conductive polymer) the necessary heating period can be substantially reduced.

Physiologically, the process of coagulation is highly dependent on the temperature at which it takes place. Under normal conditions, coagulation occurs at body temperature (37° C.), which is optimal for the proper enzymatic action of the clotting factors in the cascade.

Blood can be warmed from its incoming temperature, ranging between 18° C. and 37° C., to an arbitrary or desired temperature, such as body temperature, of 37° C. by passing through a serpentine channel in close proximity to a heater block. To accomplish the heating in a short time over a short path the block can be warmed to almost 60° C. when the incoming blood is at the lower end of its temperature range. The temperature of the blood can also be measured and the heater block can optionally be adjusted to a temperature, ranging from 40° C. to 58° C.

To measure the temperature, a sensor can be incorporated in the system 300 (FIG. 5) or in the cartridge. Optionally, a thermistor or thermocouple placed in physical contact with the cartridge or blood and an IR thermometer is pointed at the cartridge or blood. In either case the cartridge may incorporate a small well through which the incoming blood passes, rather than having direct contact with the blood. When the cartridge's material (polystyrene) is thin and the blood is kept moving through the well, then the larger heat capacity of the blood ensures the well's wall temperature is close to that of the blood. Optionally, a window allowing the passage of IR is used. The window can comprise a thin layer (e.g. 20 um or less) of polyethylene or polystyrene.

Temperature changes can occur in the body due to fever or in hospital settings such as the emergency room (ER) or operating room (OR). Trauma patients arriving at the ER are treated with large volumes of intravenous saline, which lowers body temperature to as much as 17° C. In the OR, patients undergoing cardiac bypass surgeries (CPB) have their entire blood volume pass through a lung-heart machine, which also lowers blood temperature and can adversely affect coagulation. Also, if there is a lag of time between the time of blood draw and the measurement, the temperature of blood is given time to change.

Figure 11:
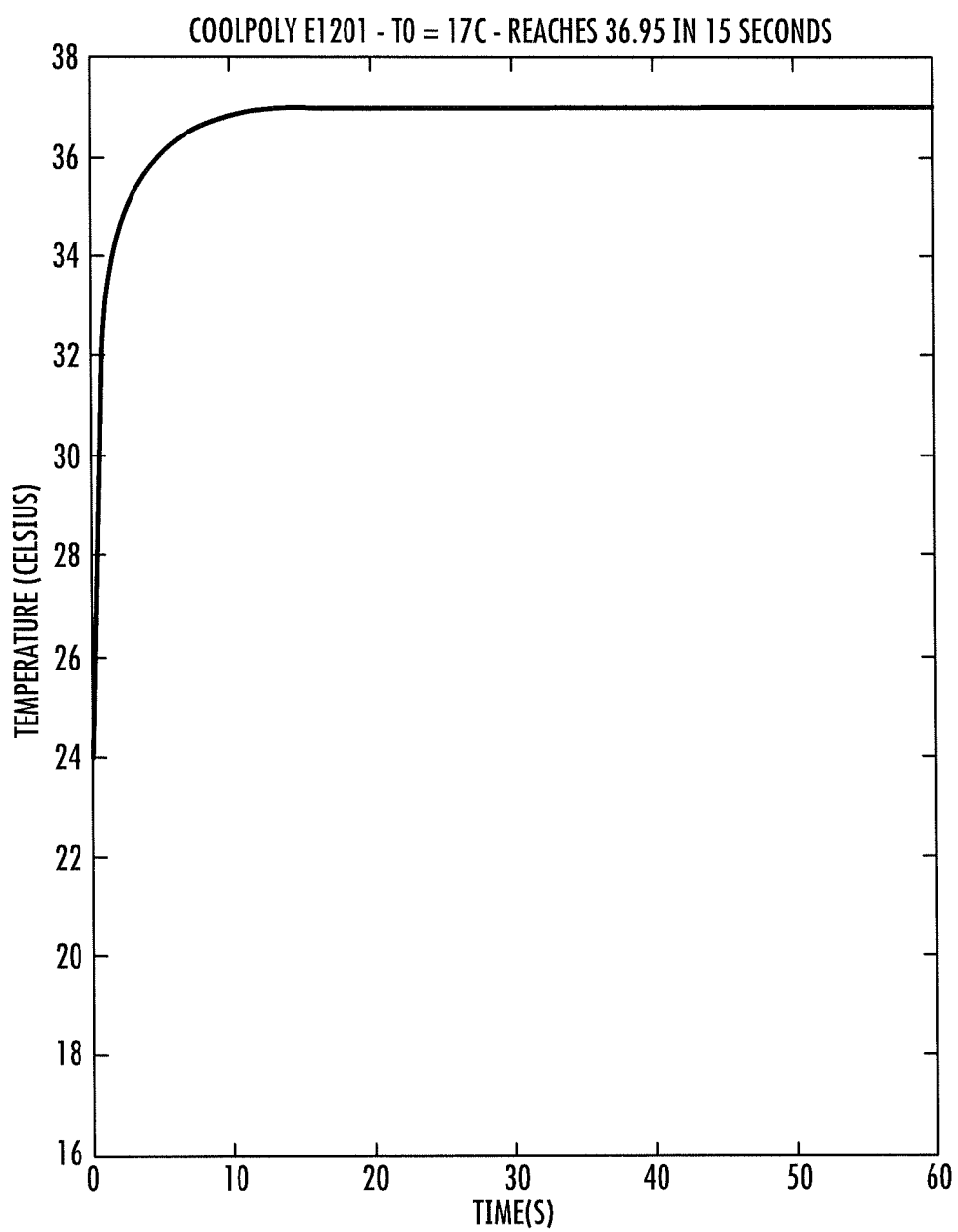
FIG. 11 is a graph showing data of heating of blood within an example cartridge for evaluating hemostasis.

Styron® 666 (Styron Inc. Berwyn, Pa.) polystyrene and the microfluidic heat exchanger channel 204 allows a blood sample to be warmed by a copper block outside of the cartridge that is kept at a constant 37° C. When a sample enters the cartridge at temperatures substantially lower than 37° C., it is optionally desirable to use a cartridge modified to allow for more rapid heating of the biological sample. For example, in a model that simulates the temperature changes over time of blood entering the polystyrene cartridge at 17° C., Styron® 666 was found to reduce ability to heat blood and the blood exiting the heat exchanger did not reach 37° C. These shortcomings of Styron® 666 are due to its relatively low thermal conductivity. When more rapid or efficient heating of the biological sample is desired than is possible through Styron® 666, the cartridge can include materials with higher thermal conductivity than Styron® 666. For example, a thermally conductive polymer (E12010) from Cool Polymers Inc. (North Kingstown, R.I.) with improved thermal conductivity properties can be used. This polymer can form a portion of the cartridge between the heating block and the channel 204. By using this polymer in a portion of the cartridge between the heating block and sample, the sample can be more efficiently heated. For example, FIG. 11 shows that in a cartridge comprising this material blood entering the heat exchanger at 17° C. reaches 37° C. within 15 seconds.

Cartridges optionally include both materials, E1201® and Styron® 666, in order to improve the heat transfer to the sample with E1201® on the heated side while maintaining flow visibility on the other side of the consumable with the Styron® 666. Another alternative is to use E1201® as an insert that fits over the copper heater and into a chassis made out of Styron® 666. This is optionally accomplished by overmolding the separate pieces into one single piece or affixing the E1201® to the Styron® chassis by means such as laser, ultrasonic or RF welding. Changing the geometry of the E1201® insert to fit into the larger chassis as a puzzle piece can further improve assembly of the separate parts and help seal the microfluidic flow chambers.

It may also be desirable to cool the biological fluid in the cartridge. In this example, and similar to when heating is desired, the cartridge can include materials with higher thermal conductivity than Styron® 666. For example, the thermally conductive polymer (E1201®), described above, with improved thermal conductivity properties can be used. This polymer can form a portion of the cartridge between a cooling device, such as a Peltier cooling device, and the channel 204. Using this polymer in a portion of the cartridge between the cooling device and sample, the sample can be efficiently cooled.

In the portable hemostasis device, the test chambers may optionally be thermally isolated from the various sub-systems of the portable device. For example, the battery case or active electronic circuitry may generate heat and create local hot spots. Thus, thermal isolation may be necessary in the portable unit. Temperature control of the sample may optionally be achieved through use of a Peltier device embedded in the portable analyzer. For example, the consumable cartridge may contain aluminum foil, some other metal, or thermally conductive polymers to conduct heat more rapidly and with more efficiency.

Each test chamber can comprise one or more reagents useful in the analysis of one or more indices of hemostasis. Optionally, the reagents are lyophilized. Optionally, one or more lyophilized bead type reagent is used. For example, the lyophilized bead can be a LyoSphere® produced by BioLyph (Minnetonka, Minn.). A self-contained lyophilized bead is a format that allows for immunochemical and clinical chemistry reagents requiring two or three components that are incompatible as liquids because of their pH level or reaction to one another to coexist compatibly. Because such lyophilized beads are stable and nonreactive, chemicals can be packaged together in the same test chamber.

To produce lyophilized reagents, a lyophilizer device can be used. For example, the reagent for a given test chamber can be frozen to solidify all of its water molecules. Once frozen, the product is placed in a vacuum and gradually heated without melting the product. This process, called sublimation, transforms the ice directly into water vapor, without first passing through the liquid state. The water vapor given off by the product in the sublimation phase condenses as ice on a collection trap, known as a condenser, within the lyophilizer's vacuum chamber. Optionally, the lyophilized product contains 3% or less of its original moisture content. The lyophilized product, which may be a pellet, can then be positioned in each test chamber. Once placed in a test chamber, the test chamber can be sealed to prevent unwanted rehydration of the product.

To locate the lyophilized reagents in the test chambers, the components can first be lyophilized and then the resulting lyophilized product can be placed in the test chambers. Using UV cure epoxy glue or a welding process (such as ultrasound or RF welding), the lens assembly is sealed over each of the test chambers. The assembled cartridge can be sealed in a vapor proof barrier (e.g. a bag) and the vapor barrier can be sealed to preserve the dehydrated nature of the product in the test chambers. When ready for use, the cartridge can be removed from the bag or vapor barrier and placed into an analysis system 300, which is described in further detail below.

Anti-static treatment of plastic cartridges is optionally used with the lyophilized reagents. Lyophilized reagents are inherently devoid of water, granting them significant electrical insulation.

Materials that are electrical insulators more readily build up static charge than materials that act as electrical conductors. This can create problems with process control when assembling the cartridges and loading the reagents. Since the cartridges are optionally made from an electrically insulating material (polystyrene, for example), it is not likely to dissipate a static charge build up within the lyophilized reagents. As a result, lyophilized reagents can statically adhere to the interior walls of the consumable. In order to prevent this from occurring, three techniques are optionally implemented to remove static build-up.

Air ionization is a method that passes directed, ionized air over a target material to neutralize residual static charge on the material surface. Directing ionized air at one or more cartridge test chamber and/or the reagents during the assembly process improves manufacturability by reducing the adherence of the reagent bead to the cartridge test chambers.

A second method implements cartridge construction using a plastic material that exhibits significantly more conductivity than standard injection molding materials. RTP PermaStat® (Winona, Mass.) plastics are an example of such materials. The use of this material for the cartridge reduces the adhesion of the lyophilized reagents to the cartridge test chamber walls.

Third, anti-static, liquid sprays are used to temporarily create a dust-free coating on optical lenses and equipment. These sprays reduce static charge on the target surface and are useful for static reduction during the cartridge assembly process.

Figure 10A:
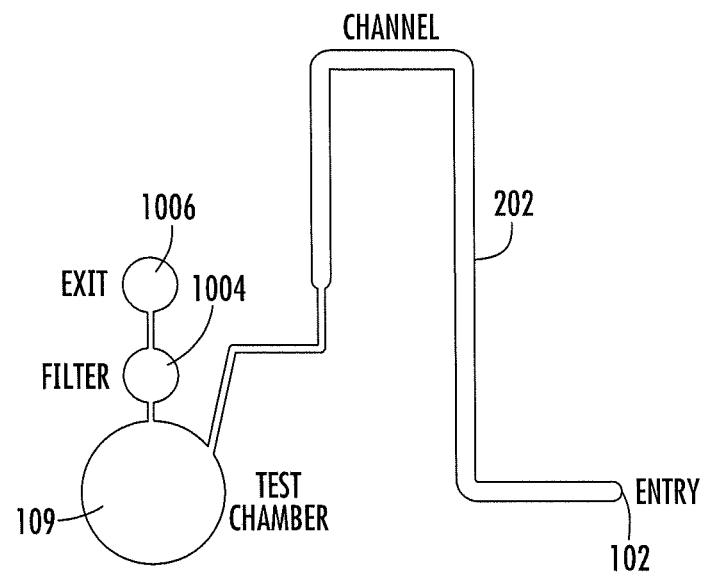
FIGS. 10A and 10B are schematic illustrations of an example sample flow pattern for use with the described devices and systems and of an example cartridge for evaluating hemostasis.

When the lyophilized reagents are exposed to the fluid sample, they can generate foam that floats at the surface of the sample in the test chambers. As illustrated in FIGS. 10A and B, the consumable cartridge 1002 optionally comprises a fluidic circuit 202 that delivers the sample from an external vessel, such as a syringe or vacutainer, into one or more test chambers (110, 112, 114, 116), where measurements are performed. The consumable may optionally include a pocket to hold the reagents within a specific geometrical location with respect to the incoming fluid flow.

FIG. 10A shows an example fluidic circuit that can be implemented in a consumable cartridge 1002. This circuit includes an entry port 102, a channel 202, at least one test chamber (110, 112, 114, 116), a filter 1004 and an exit port 1006. The biological sample can be delivered within the chamber by applying a vacuum at the exit port, with the filter allowing air to escape but stopping the fluid. A variety of different reagents can be placed within the test chamber, for example, as described throughout. In order to generate accurate measurements, the reagents are mixed within the sample before testing is initiated. For example, ultrasound emitted into the test chambers can be used to mix the reagents with the sample as described below.

Figure 10B:
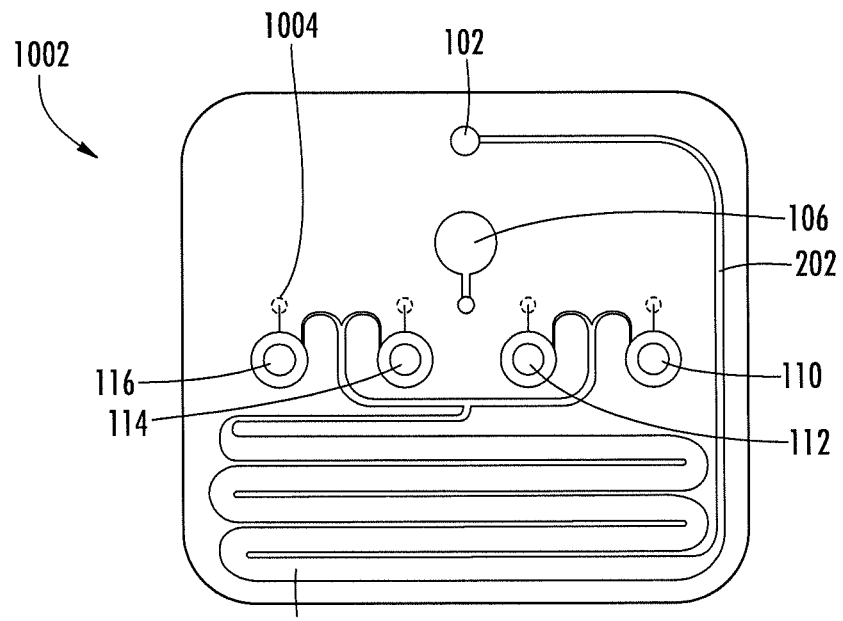

As shown in FIGS. 10A and 10B, to improve mixing of the foam, a biological fluid sample can flow through the channel 202, which enters the test chamber at the side on a tangent to the chamber. Furthermore, the change in channel diameter from large to small increases the flow velocity (conservation of flow rate) at the entrance to the test chamber. This high flow velocity, in collaboration with gravity, helps generate a re-circulating rotational flow pattern that improves mixing and reagent dispersion with the sample. As the flow enters from the side, it causes any formed foam to be pulled into the flow stream and pushed below the surface.

FIG. 10B shows a flow pattern implemented in a consumable cartridge designed for injection molding. The fluidic circuit has been repeated four times in order to deliver the sample and mix reagents in four different test chambers. The circuit presented in FIG. 10B also includes a serpentine heat exchanger to adjust the temperature of the incoming sample to a desired level.

Reagents are mixed with the sample before testing is initiated. Mixing of the reagents can be accomplished using passive and/or active mechanisms. Passive methods include, for example, the use of serpentine channels and embedded barriers to create flow turbulence. Active methods include, for example, magnetic beads, pressure perturbation, and artificial cilia. The consumable cartridge contains a lens that focuses ultrasound energy within the sample that can be used to generate streaming and mixing. The lens, also referred to herein as a lens assembly, or sound focusing assembly, is designed using a soft material, such as a thermoplastic elastomer 134, in conjunction with a rigid substrate 132, such as polystyrene. This combination provides a dry ultrasound coupling that does not require the use of any fluid or gel couplant. Note that the same lens and ultrasound driver used for hemostasis measurement can be used in this matter to provide mixing. Increasing acoustic energy for mixing can be delivered by, for example, increasing pulse length, pulse amplitude or pulse repetition frequency.

Mixing can also be provided by a variable magnetic field applied by a series of coils placed outside a test chamber or each test chamber. A small magnetic bead or magnetic stirrer can be placed within a test chamber and when the fluid sample enters the chamber, the current across the coils can be modulated in order to generate a variable magnetic field. This generates motion of the magnetic bead or magnetic stirrer, which in turns generates mixing of the sample with the reagent.

The exposure of blood to surface proteins, such as in the case of collagen or von Willebrand factor (vWF) on damaged blood vessel walls is an essential part of the coagulation process. These proteins not only contribute to the clotting cascade but also modulate several steps leading to clot formation and hemostasis.

Although exposure to these proteins is essential to the coagulation cascade, standard point-of-care (POC) coagulation assays and devices fail to take this interaction into account. Optionally, the test well(s) and/or channel(s) of a consumable cartridge, such as those described herein, are coated with such surface proteins for the measurement of coagulation within a POC medical device.

The use of surface protein coatings includes collagen, vWF, fibronectin and any other molecule that modulates coagulation such as fibrinogen and thrombin. A layer of protein on a substrate (glass, polystyrene, polypropylene) creates binding sites that allow the mediation of receptor-ligand interactions between the substrate and other biological materials such as blood in a manner that improves the assessment of coagulation or provides new testing information.

The interior surfaces of a consumable cartridge can be coated using for example: (1) a layer of such proteins by covalent binding using linker molecules, (2) covalent binding using photochemistries or (3) simple protein adsorption. Linker molecules such as streptavidin or avidin and biotin can be used for this purpose. With linker molecules, the surface of any interior portion of the cartridge that will be exposed to the biological sample is biotinylated (coated with a layer of biotin) using commercially available biotin that is conjugated to a reactive group that non-specifically and covalently binds with the substrate. A solution with a high concentration of streptavidin or avidin, which have high affinity for biotin, is added to create a layer of streptavidin/avidin bound biotin. Addition of biotinylated protein (collagen, vWF, fibronectin, thrombin, fibrinogen) then creates a layer of protein bound to the test well surface that specifically affects coagulation through interactions with plasma proteins and platelets.

Protein adsorption can be accomplished by filling the wells with a highly concentrated protein solution. Adsorption to the plastic surface takes place almost immediately depending on temperature, pH, surface charges, surface morphology and chemical composition. The solution can then be removed and the surface air dried. Brushing a highly concentrated protein solution on the surface of the wells or dipping the wells into such a solution will accomplish the same purpose.

The concentration of molecules in the solutions used for coating, whether using linker proteins or adsorption, can be changed to modulate the amount of protein that binds the substrate and, thus, modulate the effects on the coagulation cascade in a way that is relevant to physiology and hemostasis.

Referring again to FIG. 1F, to seal each test chamber, e.g. test chamber 116, a lens assembly 131 includes a rigid substrate 132 and a couplant 134 that can be positioned at the back end of each test chamber. Each couplant 134 comprises an elastomeric material. Optionally, the elastomeric material is a thermoplastic elastomer (TPE). Example elastomeric materials optionally include Dynaflex D3202, Versaflex OM 9-802CL, Maxelast S4740, RTP 6035. Optionally the couplant is over-molded to the rigid substrate.

Between each couplant 134 and the open space of each test chamber is a rigid substrate 132. The rigid substrate and the couplant form an interface that focuses ultrasound transmitted (e.g. lens assembly) by an ultrasonic transducer into the chamber's open space and onto any biological fluid and/or reagents in the chamber. The rigid substrate of the lens can comprise a material which allows sound to pass and that can act to focus ultrasound at some level within the space. Optionally, the rigid substrate comprises a styrene, such as, for example Styrene® 666.

The lens assembly may be glued or welded to the surface 101 to secure the lens in place in an orientation that allows the desired focusing of sound. Alternatively, the lens assembly is optionally manufactured together with the surface 101. In this regard, the rigid substrate 132 can be molded with the surface 101 and the couplant 134 can be overmolded on the rigid substrate. A wide variety of materials can be used to construct the device. For example, plastics can be used for single use, disposable cartridges.

Each test chamber (116, 114, 112 and 110) can have a lens assembly positioned over the large opening of each chamber's open space. In this way, each chamber can be separately interrogated by focused ultrasound.

When placed in the analysis system 300, the couplant 134 can be placed in acoustic communication with a transducer for supplying ultrasound through the lens assembly and into a test chamber. Optionally, an intermediate layer of an acoustically permeable material is positioned between an ultrasonic transducer and the couplant. For example, an intermediate layer or block of Rexolite® can be used. The intermediate layer can be forced against the couplant and can be in acoustic contact with the transducer.

Sound generated by a transducer passes through the intermediate layer, through the couplant, through the rigid substrate, and is focused within the biological sample and reagent in the test chamber. Some of the sound directed into chamber contacts the distal interior surface 111 of the test chamber, which is defined by the surface 126. Optionally, the surface is polystyrene. The distal interior surface has a known geometry and is positioned at a known distance from the ultrasound source. The distal interior surface 111 is used as a calibrated reflector, which is used to estimate the speed of sound and attenuation of sound in a test chamber at base line and during the process of clot formation and clot dissolution. These measurements can be used, for example, to estimate hematocrit of the subject along with the indexes of hemostasis. The sound generated by the transducer can be focused within the biological sample in a test chamber using a parabolic mirror that is coupled to the biological sample using an elastomer.

Figure 12A:
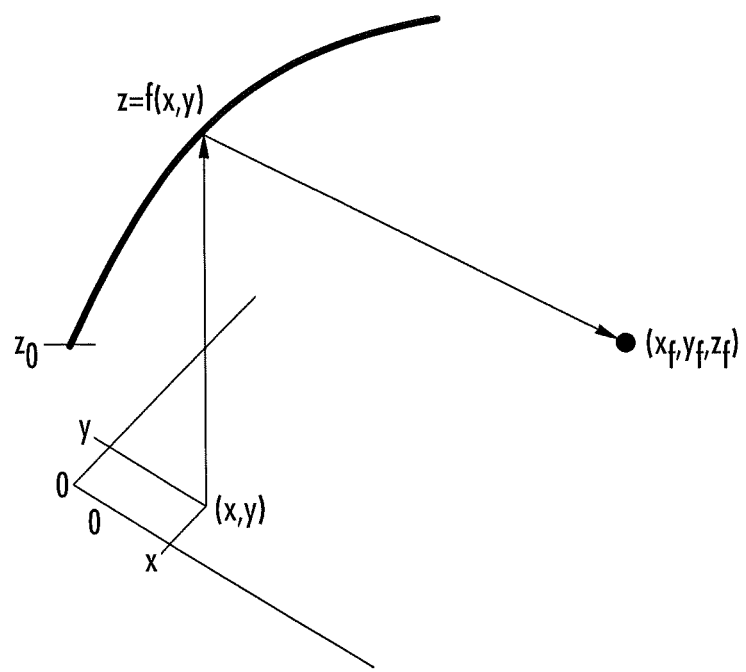
FIGS. 12A-C are schematic illustrations of example sound focusing mechanisms.

FIG. 12A illustrates an example geometry for a parabolic mirror that can be used to focus sound into one or more test chamber, wherein $f(x,y)$ is the shape of the focusing reflector, $z_0$ is the height of the reflector above the active element at the origin, and $(x_f, y_f, z_f)$ is the coordinate of the focal point. The focusing reflector is defined by a curve which is equidistant from the emitting point on the active acoustic element and the focal point. This can be expressed as:

$$d = f(x,y) + \sqrt{(x_f - x)^2 + (y_f - y)^2 + (z_f - f(x,y))^2} \quad (1)$$

Where d is the total distance from the face of the acoustic source to the focus. If the distance is set from the origin to the reflector as $z_0$, then the total path-length is:

$$d = z_0 + \sqrt{x_f^2 + y_f^2 + (z_f - z_0)^2} \quad (2)$$

The shape of the reflector can be determined by solving for $f(x,y)$ as follows:

$$d = f(x, y) + \sqrt{(x_f - x)^2 + (y_f - y)^2 + (z_f - f(x, y))^2} \quad (3)$$

$$d - f(x, y) = \sqrt{(x_f - x)^2 + (y_f - y)^2 + (z_f - f(x, y))^2} \quad (4)$$

$$(d - f(x, y))^2 = (x_f - x)^2 + (y_f - y)^2 + (z_f - f(x, y))^2 \quad (5)$$

$$d^2 - 2df(x, y) + f^2(x, y) = (x_j - x)^2 + (y_f - y)^2 + z_j^2 - 2z_f f(x, y) + f^2(x, y) \quad (6)$$

$$d^2 - 2df(x, y) = (x_f - x)^2 + (y_f - y)^2 + z_f^2 - 2z_j f(x, y) \quad (7)$$

-continued $$2z_f f(x, y) - 2df(x, y) = (x_j - x)^2 + (y_f - y)^2 + z_j^2 - d^2 \quad (8)$$

$$f(x, y)(2z_j - 2d) = (x_f - x)^2 + (y_f - y)^2 + z_f^2 - d^2 \quad (9)$$

$$f(x, y) = \frac{(x_f - x)^2 + (y_f - y)^2 + z_f^2 - d^2}{2(z_j - d)} \quad (10)$$

Figure 12B:
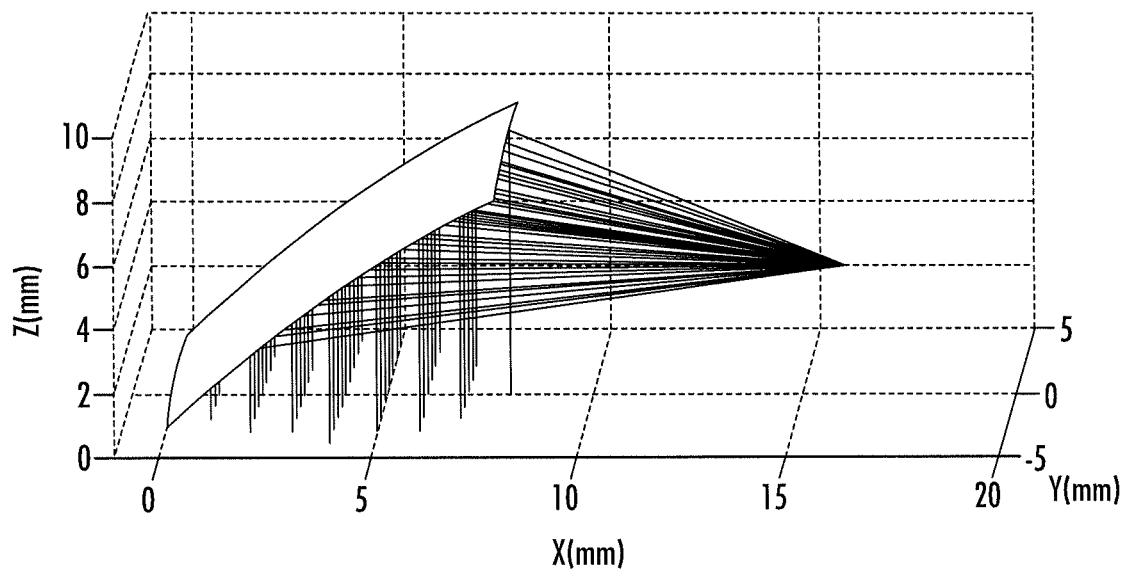
Figure 12C:
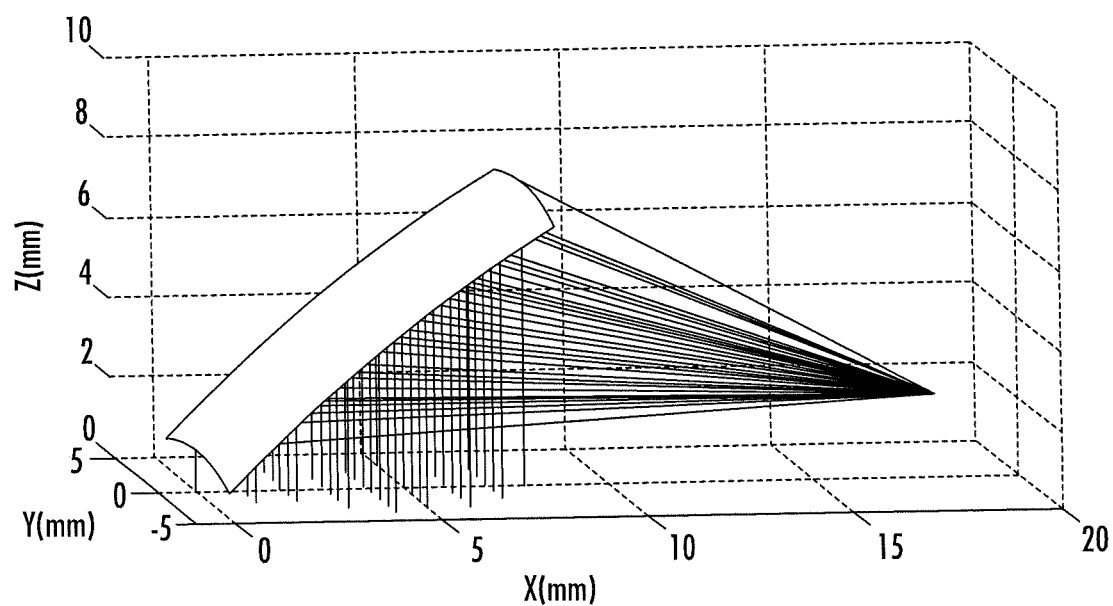

If $z_0$ is set, then the equation 2 above can be evaluated and substituted into equation 10 above to yield an equation for the surface of the reflector. The reflector is a parabolic section. Example parameters are optionally an 8 mm aperture with a focus at 16 mm laterally, 4 mm in range and with an offset between the mirror and aperture of 0.5 mm. A diagram of this geometry is shown in FIG. 12B. This geometry is useful where the focusing mirror is placed within the system. The mirror can also be placed within the cartridge. In this case, the focus is optionally moved closer in the axial dimension, but further in the lateral dimension as shown in FIG. 12C.

Figure 4:
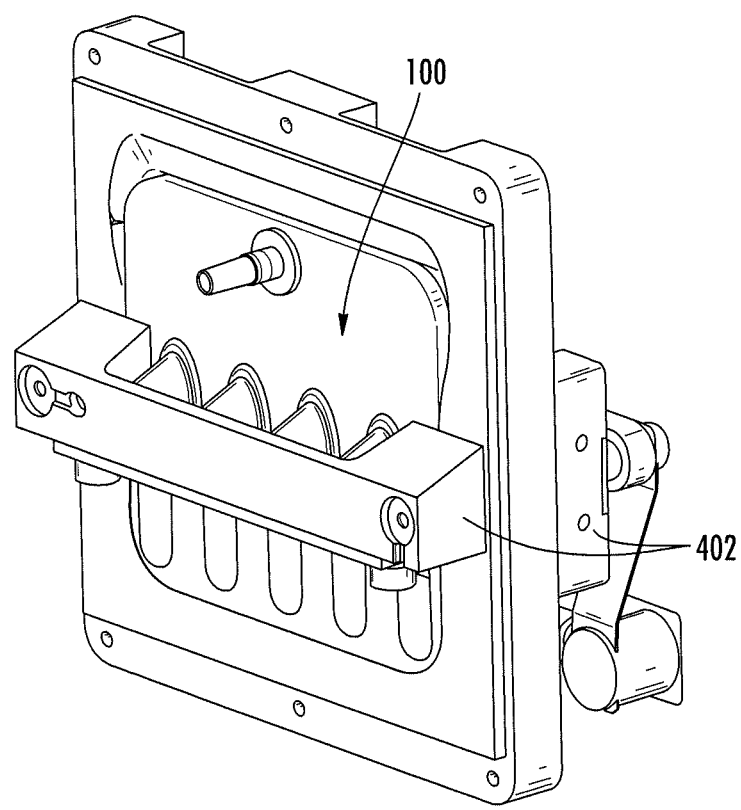
FIG. 4 is a schematic illustration of a portion of a system for evaluating hemostasis.

The cartridge 100 can be positioned into pocket 302 of an analysis system 300. As shown in FIG. 4, the pocket includes an actuator system 402 for pressing the intermediate layer, such as Rexolite®, that is acoustically coupled to a transducer into contact with the couplant 134. In this way the pocket holds the cartridge securely in place and in an orientation such that ultrasound can be focused into each testing chamber.

Figure 5:
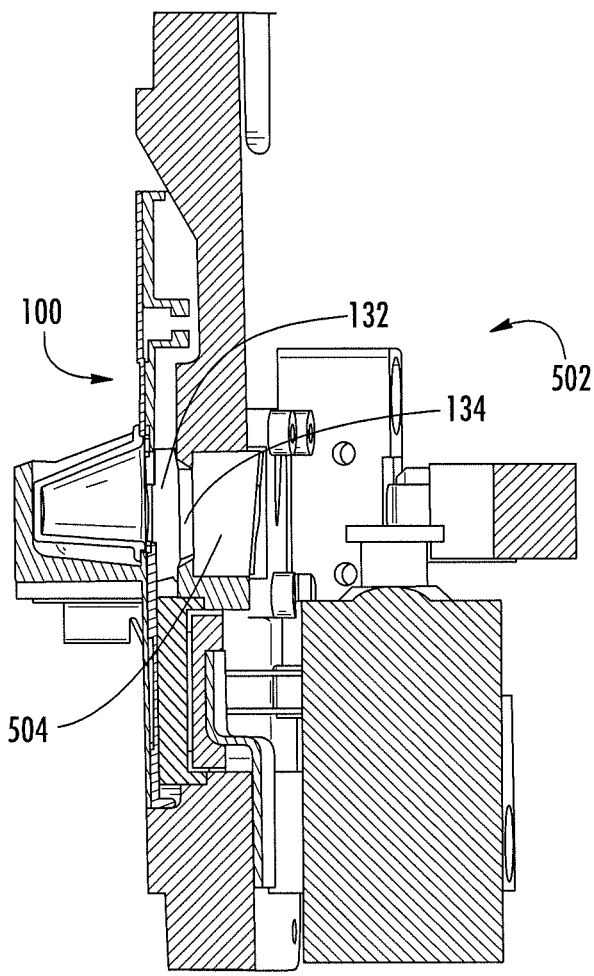
FIG. 5 is a schematic illustration of a portion of a system for evaluating hemostasis.

FIG. 5 shows further aspects of the cartridge 100 positioned in the analysis system. The cartridge is positioned such that the intermediate layer 504 is pushed into the couplant 134, which is in communication with the rigid substrate 132 of the lens assembly 131. Ultrasonic generating means 502, including at least one ultrasonic transducer, are positioned such that ultrasound is transmitted through the intermediate layer, lens assembly, and into the test chamber.

At least a portion of the sound is reflected by the biological sample positioned therein the chamber, and a portion of the sound transmitted into the chamber can also be reflected from the chamber distal surface 111. The reflected ultrasound can be received by the ultrasonic transducer and transmitted to the system for processing. Thus, the cartridge and the analysis system 300 may be in communication such that data and other operational or processing signals may be communicated between the cartridge and the analysis system.

A suitable analysis system 300 can therefore comprise one or more processing devices. The processing of the disclosed methods, devices and systems can be performed by software components. Thus, the disclosed systems, devices, and methods, including the analysis system 300, can be described in the general context of computer-executable instructions, such as program modules, being executed by one or more computers or other devices. Generally, program modules comprise computer code, routines, programs, objects, components, data structures, etc., that perform particular tasks or implement particular abstract data types. For example, the program modules can be used to cause the transmission of ultrasound having desired transmit parameters and to receive and process ultrasound to evaluate hemostasis indices of a sample from the subject. The software can also be used to control the heating of the biological sample using the heat exchanger and to monitor and indicate the fill level of a given chamber. The processor can also be used to perform algorithms, to determine hemostatic indices and hematocrit. In some examples, the software can be used to back-out determined hematocrit from determined hemostatic indices. The determined hemostatic indices and hematocit can be displayed to a medical professional or medical agent for the purpose of making medical decisions for a subject.

Figure 1G:
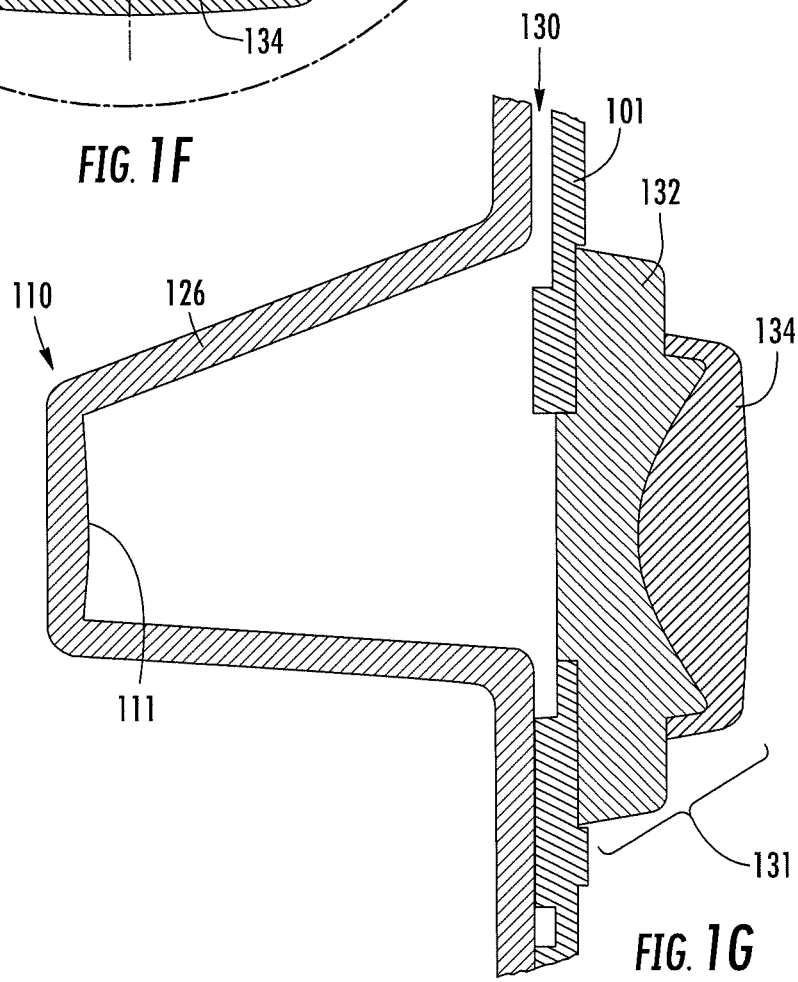

Referring to FIG. 1G, an example consumable cartridge for use in a portable hemostatic analyzer is shown. An acoustic lens 132 and couplant 134 are positioned at the back end of each test chamber 109 of a consumable cartridge. Each couplant 134 comprises an elastomeric material. For example, the elastomeric material is a thermoplastic elastomer (TPE). The lens and the couplant form an interface that focuses ultrasound transmitted by an ultrasonic transducer into the chamber's open space and onto any biological fluid and/or reagents in the chamber. The lens can comprise a material which allows sound to pass and that can act to focus ultrasound at some level within the space. For example, the lens may comprise styrene, such as styrene 666. The lens may be glued or welded to the rear surface 126 to secure the lens in place in an orientation that allows the desired focusing of sound.

A wide variety of materials can be used to construct the portable device and facilitate compact construction and portability. For example, plastics can be used for single use, consumable cartridges. Each test chamber (116, 114, 112 and 110) can have a lens and couplant positioned over the large opening of the each chamber's open space. In this way, each chamber can be separately interrogated by focused ultrasound.

The overall dimension of the lens is dependent upon the relative acoustic properties (e.g., the speed of sound) of components 132 and 134. A large difference in speed of sound between 132 and 134 allows creation of a thin lens. A small difference in speed of sound results in a thicker lens. For example, the combination of a thermoplastic elastomer (TPE) and styrene 666 generates a thin lens with axial thickness of 4.5 mm or less.

The axial length of the test chamber is generally dependent upon the F # (defined as the focal length divided by the diameter of the ultrasound transducer) of the device. Using a transducer with a diameter of 7.5 mm and an F # of 1.5, the axial length of the blood-filled chamber 110 is 11 mm or less.

Some of the sound directed into chamber contacts the distal interior surface 111 of the test chamber, which is defined by the surface 126. The surface 126 may be constructed of a polystyrene material. The distal interior surface has a known geometry and is positioned at a known distance from the ultrasound source. The distal interior surface 111 is used as a calibrated reflector, which is used to estimate the speed of sound and attenuation of sound in a test chamber at base line and during the process of clot formation and clot dissolution. These measurements can be used, for example, to estimate hematocrit of the subject along with the indexes of hemostasis. The thickness of the plastic wall defining the surface 126 is about 1 mm to 2 mm, but may be less for materials having similar acoustic properties but higher strength to contain and support the blood sample.

Figure 13:
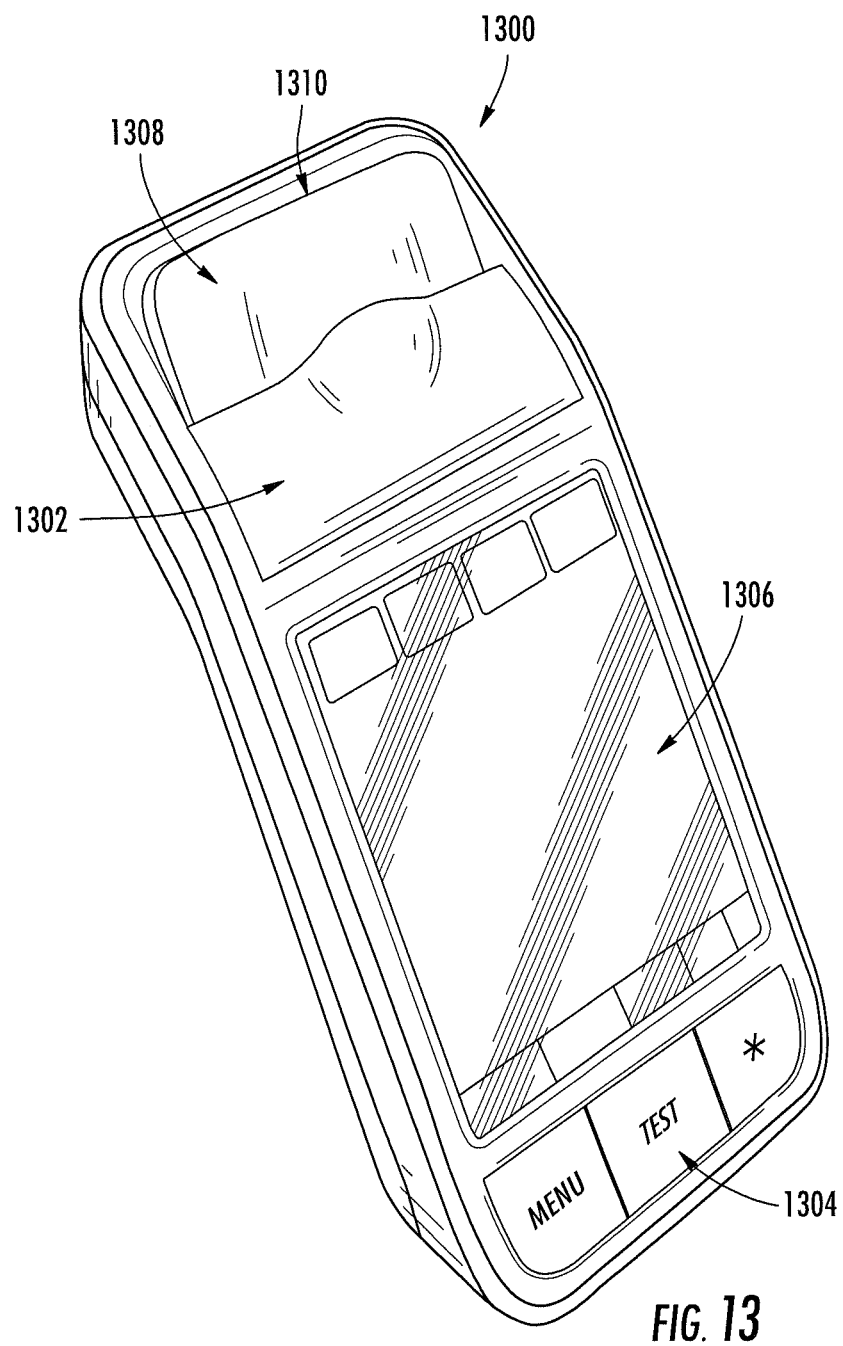
FIG. 13 is a schematic illustration of an example portable hemostasis analyzer.

Referring now to FIG. 13, a compact and portable hemostasis analyzer is presented which uses sonorheometry to characterize hemostasis. This system 1300 has a receptacle 1310 configured to receive a consumable cartridge 1308. A clamping mechanism 1302 places the consumable 1308 in contact with the ultrasound transducer. When a consumable cartridge 1308 is placed in the analysis system, the couplant 134 can be placed in acoustic communication with a transducer for supplying ultrasound through the lens and into a test chamber.

The system shown in FIG. 13 can use a single piezoelectric disk that is only 220 microns or less thick. Optionally, an intermediate layer of an acoustically permeable material may be positioned between the ultrasonic transducer and the couplant 134. For example, an intermediate layer or block of Rexolite® can be used. The intermediate layer can be forced against the couplant and can be in acoustic contact with the transducer. This intermediate layer of material can be very small in order to preserve the structural integrity of the component. In the case of Rexolite®, a thickness between 5 mm and 6 mm can be used, for example.

Sound generated by a transducer (220 microns) passes through the intermediate layer (5 mm), through the couplant (2.5 mm) and polystyrene (2.0 mm), which together form the lens (4.5 mm total), and is focused within the sample and reagent in the test chamber (11 mm length plus 1 mm thickness of the wall defining the surface 126). Thus, the hemostatic analyzer may have a thickness of about 26.5 mm, such as 25 mm or even less, plus desired housing thicknesses, depending upon selection of tradeoffs in materials costs, ruggedness and performance. Generally, it is expected that the volume of at least these minimal operational components is 60 cubic inches or less based on a 2.5 inches by 6 inches by 4 inches rectangular boundary that would contain the components.

Advantageously, the hemostasis analyzer disclosed herein facilitates portable use with a compact size that is less than the 7 inch (17.78 cm) minimum dimension of prior art multiple hemostatic parameter measurement devices confined largely to use on a bench top. For example, even the largest dimension of the hemostatic analyzer disclosed herein need not be substantially more than 15 cm, smaller than the smallest dimension of prior art multiple parameter devices. And, the smallest dimension (e.g., a thickness) of the hemostasis analyzer may be 15 cm, 10 cm, 7 cm, 5 cm, 4.4 cm, 4 cm, 3 cm, down to 2.5 cm or even smaller, as described above.

Furthermore, the design of the consumable cartridge is such that no air-blood interface is present. The blood is completely sealed within the consumable in a chamber that is mostly full or completely full with blood. For example, a vacuum may draw blood from an external syringe into the consumable and the consumable may include a filter that allows air to pass out of the consumable but not blood. In a more portable system, the user may attach a syringe and fill the consumable by pushing the plunger of the syringe with filters allowing escape of the air but no blood. This avoids air splashing and greatly reduces effects of external environmental vibrations, which might corrupt the measurements. A sample which has an open air/blood interface is subject to large magnitude surface motion when test instrument is moved or displaced by environmental vibration. Eliminating the open surface makes the system much more robust to environmental vibration. The hydrophobic filters within the consumable cartridge may be optically observed to determine when filling is complete. Once complete filling has occurred, the hydrophobic filters may change colors, optionally from white to red.

Advantageously, preliminary assessments show that not only is the hemostasis analyzer compact in dimensions, a full production version is expected to be substantially lighter than the next lightest full analyzer capable of measuring multiple hemostatic parameters. For example, the hemostasis analyzer may be a total of 12 pounds or 10 pounds or less.

Thus, one skilled in the art will appreciate that the systems, devices, and methods disclosed herein can be implemented via a general-purpose computing device in the form of a computer. The computer, or portions thereof, may be located in the analysis system 300. The components of the computer can comprise, but are not limited to, one or more processors or processing units, a system memory, and a system bus that couples various system components including the processor to the system memory. In the case of multiple processing units, the system can utilize parallel computing.

The computer typically comprises a variety of computer readable media. Exemplary readable media can be any available media that is accessible by the computer and comprises, for example and not meant to be limiting, both volatile and non-volatile media, removable and non-removable media. The system memory comprises computer readable media in the form of volatile memory, such as random access memory (RAM), and/or non-volatile memory, such as read only memory (ROM). The system memory typically contains data such as data and/or program modules such as operating system and software that are immediately accessible to and/or are presently operated on by the processing unit.

In another aspect, the computer can also comprise other removable/non-removable, volatile/non-volatile computer storage media. By way of example, a mass storage device, which can provide non-volatile storage of computer code, computer readable instructions, data structures, program modules, and other data for the computer. For example and not meant to be limiting, a mass storage device can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device, including by way of example, an operating system and software. Each of the operating system and software, or some combination thereof, can comprise elements of the programming and the software. Data can also be stored on the mass storage device. Data can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer via an input device. Examples of such input devices comprise, but are not limited to, a keyboard, pointing device (e.g., a "mouse"), a touch screen, a scanner, and the like. These and other input devices can be connected to the processing unit via a human machine interface that is coupled to the system bus, but can be connected by other interface and bus structures, such as a parallel port, game port, an IEEE 1394 Port (also known as a Firewire port), a serial port, or a universal serial bus (USB).

In yet another aspect, a display device 304, such as a touch screen, can also be connected to the system bus via an interface, such as a display adapter. It is contemplated that the computer can have more than one display adapter and the computer can have more than one display device. For example, a display device can be a monitor, an LCD (Liquid Crystal Display), or a projector.

Any of the disclosed methods can be performed by computer readable instructions embodied on computer readable media. Computer readable media can be any available media that can be accessed by a computer. By way of example and not meant to be limiting, computer readable media can comprise computer storage media and communications media. Computer storage media comprise volatile and non-volatile, removable and non-removable media implemented in any method or technology for storage of information such as computer readable instructions, data structures, program modules, or other data.

Example 1

The reagents in each test chamber, also referred to as a test well, can include all the reagents needed for evaluating one or more indices of hemostasis.

Optionally the cartridge is a single use, disposable cartridge with pre-loaded lyophilized reagents. The cartridge can be used with whole blood from a subject. The cartridge or assay components include the following for fresh whole blood samples. Four separate wells containing lyophilized reagents to which 1.6 mL of fresh whole blood is added. Each test well utilizes around 300 µL of fresh whole blood along with the following reagents:

TABLE 1

| Test Well 1 | Test Well 2 | Test Well 3 | Test Well 4 |
|---|---|---|---|
| 0.15 mg of kaolin buffers and stabilizers | 0.15 mg of kaolin buffers and stabilizers | 0.3 U of thrombin buffers and stabilizers | recombinant tissue factor buffers and stabilizers |
| 0 µL of 2 mg/mL abciximab | 12 µL of 2 mg/mL abciximab | 12 µL of 2 mg/mL abciximab | 0 µL of 2 mg/mL abciximab |

Figure 6A:
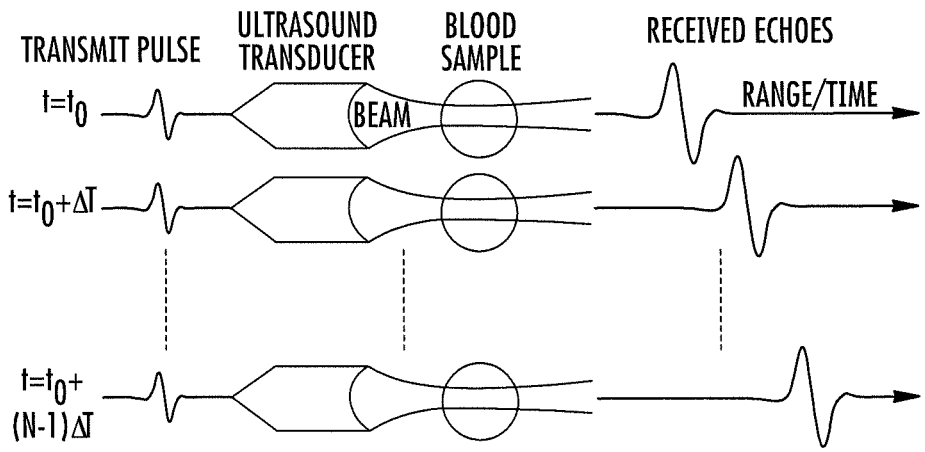
FIG. 6A is a schematic illustration showing N acoustic pulses are sent into a blood sample to generate a force. The resulting deformation can be estimated from the relative time delays between the N returning echoes.
Figure 6B:
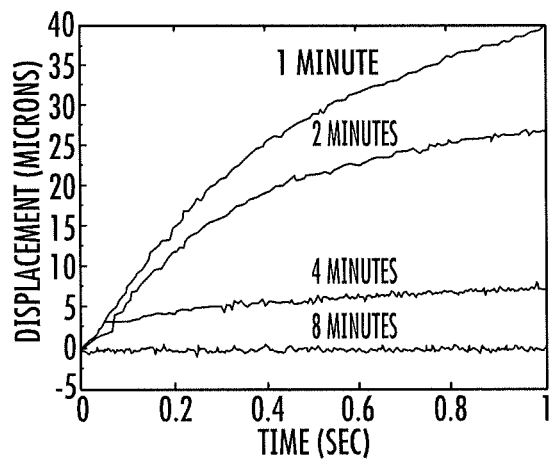
FIG. 6B is a graph showing example displacement curves generated within a blood sample. As blood clots, reduced displacement is observed.
Figure 6C:
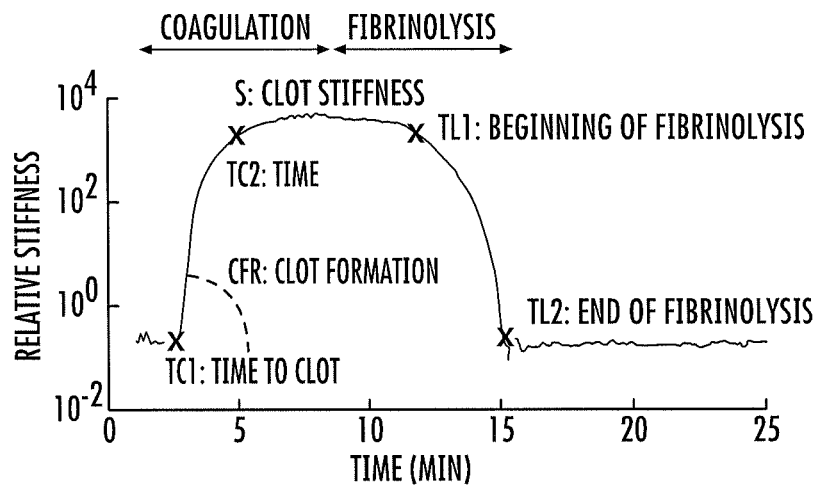
FIG. 6C is a graph showing displacements combined to form graphs of relative stiffness, which characterize the hemostatic process. The parameters described in panel are estimated from parameters found by fitting a sigmoidal curve.

The devices, systems, and methods use the phenomenon of acoustic radiation force to measure changes in mechanical properties (e.g. stiffness) of a blood sample during the processes of coagulation and fibrinolysis. These changes are representative of the role of the four key components of hemostasis: (i) plasma coagulation factors, (ii) platelets, (iii) fibrinogen, and (iv) fibrinolytic factors of the plasma. The basic approach is shown in FIGS. 6A-C.

A series of N focused ultrasound pulses are sent into a blood sample at short intervals $\Delta T$ ($\Delta T$ is on the order of microseconds), as shown schematically in panel A. Each pulse generates a small and localized force within the blood as acoustic energy is absorbed and reflected during propagation. This force, which is concentrated around the focus of the ultrasound beam, induces a small displacement within the blood sample that depends upon the local mechanical properties. These displacements are on the order of 40 microns or less at the focus of the ultrasound beam.

Each pulse also returns an echo, as a portion of its energy is reflected from within the blood sample. Because the sample moves slightly from one pulse transmission to the next, the path length between the fixed ultrasound emitter and any given region within the target increases with pulse number. This change in path length can be estimated from differences in the arrival times of echoes from the same region. The ensemble of these delays forms a time-displacement curve that holds combined information about viscoelastic properties of the sample. These time-displacement curves are shown in FIG. 6B. These time-displacement curves are measured every 6 seconds to fully characterize the dynamics of coagulation and fibrinolysis, representing the entire hemostatic process.

When the blood sample is in a viscous fluid state, the application of the acoustic force generates large displacements. As coagulation is activated and fibrinogen is cross-linked into fibrin strands, the sample behaves as viscoelastic solid and the induced displacement reduce as the stiffness of the sample increases. The interaction of platelets and the fibrin mesh also further reduce the induced displacements as the clot's stiffness increases. As the clot progresses into the phase of fibrinolysis, the fibrin mesh is dissolved by the fibrinolytic enzymes and the sample returns to viscous fluid, exhibiting increasing displacements.

The evolution of the magnitude of the induced displacements over time is therefore directly related to the changes in mechanical properties of the blood sample during hemostasis. A curve obtained with this method is shown in FIG. 6. Functional data, which highlights the role of coagulation factors, platelets, fibrinogen, and fibrinolysis can be extracted from the curve, as labeled in the FIG. 6.

Acoustic radiation force results from the transfer of momentum that occurs when a propagating acoustic wave is either absorbed or reflected. This body force acts in the direction of the propagating wave, and can be approximated by the following expression:

$$F = \frac{2\alpha \langle I(t) \rangle}{c} = \frac{2\alpha PII}{c} \frac{1}{\Delta T} \quad (1)$$

where $\alpha$[m−1] is the acoustic attenuation coefficient, c [m/s] is the speed of sound, I(t) [W/m2] is the instantaneous intensity of the ultrasound beam, PII is the pulse intensity integral, $\Delta T$ [s] is the time interval between successive ultrasound pulse transmissions, and $\langle \; \rangle$ indicates a time averaged quantity.

The acoustic energy used by the instrument to generate acoustic radiation force is comparable with the acoustic energy typically used for common medical ultrasound procedures such as color Doppler imaging. The estimated maximum acoustic intensity is on the order of 2.5 W/cm2 (time average), which results in a temperature increase of the blood sample of 0.01° C. for each measurement ensemble (performed roughly every 6 seconds).

As the blood sample rapidly changes from viscous fluid to viscoelastic solid during coagulation and back to viscous fluid after clot lysis, the applied acoustic radiation force is adaptively changed to induce displacements above the noise threshold, but below levels that could induce mechanical disruption (typically below 40 microns).

The magnitude of the force is adjusted to follow the changes in mechanical properties of the blood sample by varying the time interval $\Delta T$ between successive pulses, as shown in equation (1). The maximum displacement induced during the (m−1)th acquisition is used to determine whether the force should be increased or decreased for the mth acquisition, based on predetermined threshold values. This adaptive process allows characterization of five orders of magnitude in stiffness without generating high strain within the blood sample that could alter the dynamics of coagulation and fibrinolysis.

As shown in equation (1), the applied acoustic radiation force changes as a function of acoustic attenuation and speed of sound, both of which change as a function of coagulation. The system uses the echoes returning from within the cartridge to estimate changes in these parameters and normalize the acoustic radiation force.

Acoustic radiation force is generated using conventional piezoelectric materials that act as acoustic emitters and receivers. These materials deform when a voltage is applied across them, and conversely generate a voltage when they are deformed. Similar to optics, an acoustic lens can be placed in front of the piezoelectric material to focus acoustic energy on a single focal point.

In the example systems, method, and devices, piezoelectric disks are used that have an active diameter of 7.5 mm. The acoustic lens is provided by the curved shape of the disposable cartridge. Four disks are placed side by side to send sound in the four test wells in a disposable. The frequency of vibration of these piezoelectric disks is centered at 10 MHz, well within the range of frequencies used in conventional ultrasound imaging.

Figure 7:
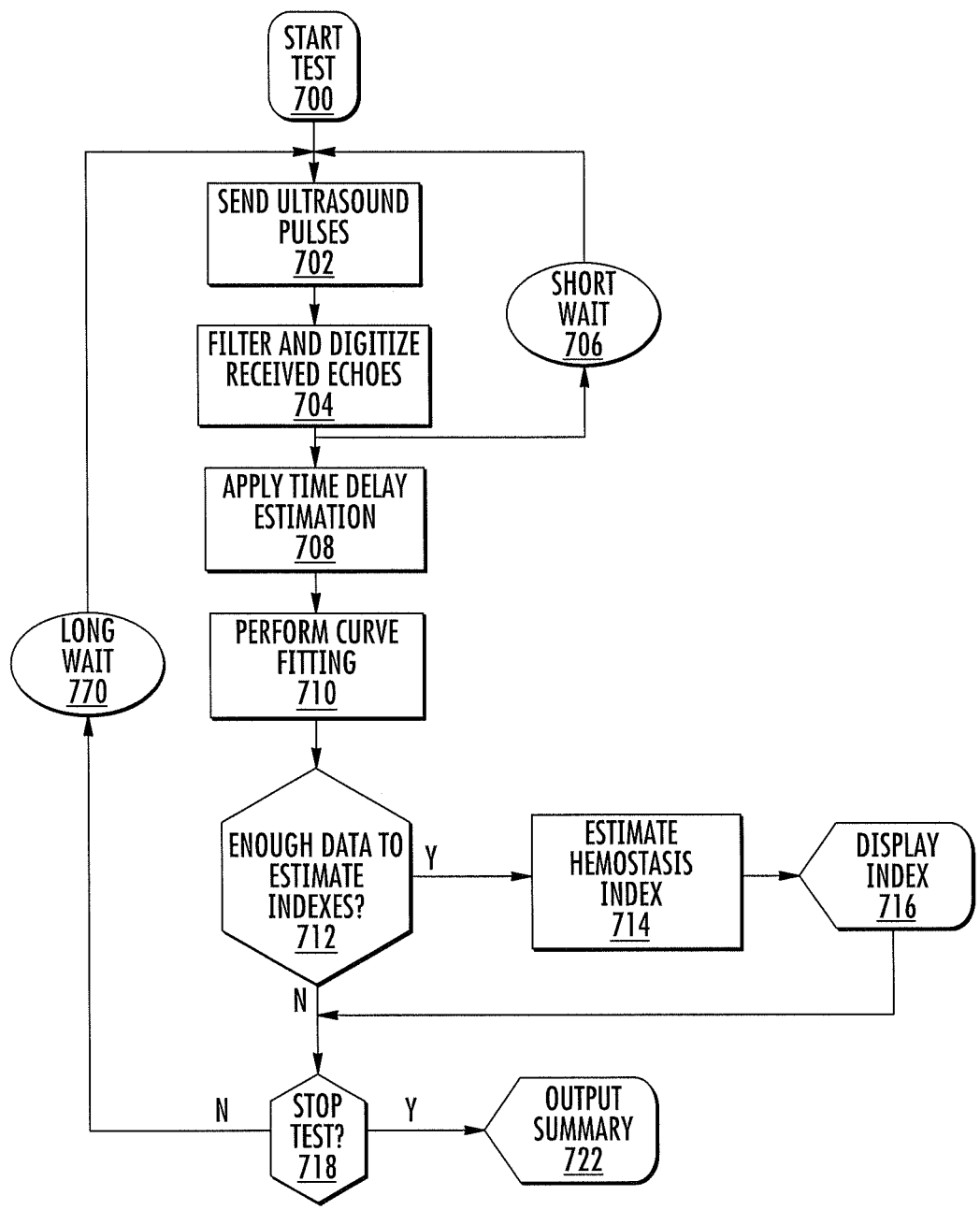
FIG. 7 is a flow diagram illustrating an example method to estimate hemostasis parameters.

Ultrasound echo signals returning to the transducers from the blood samples are first filtered to remove electronic noise, digitized, and further processed within an embedded processor in the system. A flow chart of the data analysis steps performed by the system is shown in FIG. 7 where a test starts at block 700. Ultrasound pulses are transmitted into a target sample in a test well at 702. Echoes are received, filtered and digitized at 704. After a short wait 706, steps 702 to 704 can be repeated. A time delay estimation is applied at 708 and a curve fitting at 710. The system then determines if enough data has been acquired to estimated the desired indexes of hemostasis at 712. If there is enough data to estimate a hemostasis index, the hemostasis index is estimated at 714 and displayed at 716. If at 712 it is determined that not enough data has been acquired to estimated a hemostasis index, the system determines if the test should be stopped at 718 and, if so, an output summary is generated at 722. If the test is to continue, after a long wait 770, one or more steps 702-770 are optionally repeated.

Time Delay Estimation

Once an ensemble of N pulses is sent into the blood sample and the returning echoes are obtained, time delay estimation (TDE) is performed to estimate a local time-displacement curve, similar to that shown in FIG. 6B. TDE entails measuring the relative time shift from one received echo to the next; the known value of the speed of sound in blood allows conversion of the time shifts into displacements. TDE is performed around the focus of the ultrasound beam. This process is repeated every 6 seconds (arbitrary fixed wait) to obtain time-displacement curves throughout the process of coagulation and fibrinolysis.

A variety of "off-the-shelf" algorithms are available to perform this operation. TDE is a common signal processing step in application fields ranging from RADAR, SONAR, and medical ultrasound imaging (Doppler).

Curve Fitting

The viscoelastic properties of the blood sample during hemostasis are modeled using a modified model consisting of the well-known Voigt-Kelvin mechanical model with the addition of inertia. While the dynamic changes in viscoelasticity of blood during hemostasis are certainly complex, the modified Voigt-Kelvin model is simple and robust, and it has been well validated in the past.

Each time-displacement curve is fitted to the characteristic equation of the modified Voigt-Kelvin model to estimate a variety of parameters relating to the viscoelastic properties of the sample. These parameters include relative elasticity, relative viscosity, time constant, and maximum displacement. The mathematical expression of the equation of motion for the modified Voigt-Kelvin model is $$x(t) = \quad (2)$$

$$-\frac{\xi + \sqrt{\xi^2-1}}{2\sqrt{\xi^2-1}} s \cdot e^{\left(-\xi+\sqrt{\xi^2-1}\right)\omega t} + \frac{\xi - \sqrt{\xi^2-1}}{2\sqrt{\xi^2-1}} s \cdot e^{\left(-\xi+\sqrt{\xi^2-1}\right)\omega t} + s$$

where $\xi$ is the damping ratio, $\omega$ is the natural frequency, and s is the static sensitivity.

Among the parameters obtained by the curve fitting, the system uses the estimated displacement magnitude at 1 second as a qualitative measure of the stiffness of the sample. When blood is in viscous fluid state, the displacement at 1 second is high. As the blood coagulates, this displacement decreases proportionally to the generation of the fibrin mesh and activity of platelets. The value increases again during the process of fibrinolysis.

Estimate Indices of Hemostatic Function

The displacement values obtained at 1 second for each data acquisition are compiled to form a curve showing relative stiffness as a function of time (FIG. 6C). This curve, previously shown, fully characterizes hemostasis and can be further processed to estimate direct indices of hemostatic function.

Indices of hemostasis are calculated by fitting a sigmoidal curve to the stiffness-time curve (FIG. 6C) and evaluating the first derivative of the curve. The times to clot TC1 and TC2 are calculated based on a threshold value of the derivative curve (20% of the minimum value), and are indicative of the beginning and ending phase of fibrin polymerization. The clotting slope CFR is the maximum of the derivative curve and is indicative of the rate of fibrin polymerization. The stiffness S is estimated from the stiffness curve three minutes after TC2. S depends upon platelet function and the final stiffness of the fibrin network. Identical methods and indices are calculated for the fibrinolytic process. In particular the times TL1 and TL2 can be defined to represent the initial and final phases of the fibrinolytic process and the consequent dissolution of the fibrin network (time to lysis).

A summary of the parameters generated for each test chamber is presented in the table 2:

| Parameter | Information provided | Dependent upon |
|---|---|---|
| $TC_1$, $TC_2$ | Measure initial and final fibrin formation | Function of fibrinogen and other coagulation factors |
| S | Fibrin and platelet activity | Function of fibrin network and platelet aggregation |
| CFR | Rate of fibrin polymerization | Function of fibrinogen and other coagulation factors |
| $TL_1$, $TL_2$ | Clot dissolving process | Function of fibrinolytic proteins of the plasma |

In order to isolate the four main components of hemostasis, four measurements are performed in parallel within the disposable cartridge using a combination of agonists and antagonists in each of four wells. The measurements in each well are combined to form indices of hemostasis as shown in the table 3:

| Output | Method |
|---|---|
| Coagulation factors Index (Intrinsic Pathway) | Time to clot $TC_1$ in well #1 |
| Coagulation factors Index (Extrinsic Pathway) | Time to clot $TC_1$ in well #4 |
| Platelets Index | Stiffness S differential between well #1 and well #2 |
| Fibrinogen Index | Stiffness S in well #3 |
| Fibrinolysis Index | Time to lysis $TL_1$ in well #4 |

Many modifications and other embodiments of the invention set forth herein will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system for determining a plurality of hemostatic parameters for a blood sample, the system comprising:
   a system housing;
   a receptacle defined in part by the system housing and configured to retain a single use cartridge;
   a cartridge, the cartridge configured for single-use having wells configured to hold blood samples therein, the wells defining a first test chamber, a second test chamber, and a third test chamber coupled to a respective first test channel, second test channel, and third test channel, each defined in part by a space sufficient to allow induced displacement of the blood sample in the test chamber from an application of a force applied to the blood sample to interrogate one or more viscoelastic properties of the test sample, the cartridge comprising comprises a fluid pathway having an inlet, defined by a housing of the cartridge, and from which an external vessel establishes fluid communications, to receive a test sample, wherein the fluid pathway is in fluid communication with the first test chamber, the second test chamber, and the third test chamber to deliver the test sample, or a portion thereof, to the wells, the cartridge comprising all reagents needed for evaluating indices of hemostasis to assess main components of hemostasis comprising plasma coagulation factors, platelets contribution, and fibrinogen contribution to coagulation;
   a first reagent or a first combination of reagents forming a first set of one or more lyophilized reagents pre-loaded in the cartridge, the first set of one or more lyophilized reagents being disposed along a space of the first test channel, wherein the first reagent, or a reagent included in the first combination of reagents, is configured to activate coagulation via the extrinsic pathway;
   a second combination of reagents forming a second set of one or more lyophilized reagents pre-loaded in the cartridge, the second set of one or more lyophilized reagents being disposed along a space of the second test channel, wherein the second combination of reagents includes i) a reagent, or a combination of reagents, configured to activate coagulation and ii) a reagent, or a combination of reagents, configured to inhibit platelet function; and
   a third reagent or a third combination of reagents forming a third set of one or more lyophilized reagents pre-loaded in the cartridge, the third set of one or more lyophilized reagents being disposed along a space of the third test channel, wherein the third reagent, or a reagent included in the third combination of reagents, is configured to activate coagulation via the intrinsic pathway;

a pump-mechanism configured to fill the first test chamber, the second test chamber, and the third test chamber, wherein the pump-mechanism is configured to generate a pressure that cause the one or more blood samples to move through channels of the cartridge, when the cartridge is placed in the receptacle, to the first test chamber, the second test chamber, and the third test chamber of the cartridge;

a piezo-actuated device coupled to the receptacle within the system housing, the piezo-actuated device being configured to induce vibration of the one or more blood samples in the wells to measure changes in viscoelastic properties of the blood samples over time;

an analyzer configured to receive signals associated with the one or more blood samples and to determine, based on the measured viscoelastic properties, at least two hemostatic parameters, wherein the at least two hemostatic parameters include at least two different types of parameters selected from the group consisting of the plasma coagulation factors, the platelets contribution, and the fibrinogen contribution, wherein the parameters associated with platelet contribution and fibrinogen contribution are respectively determined from an assessed clot stiffness associated with a clot formed in at least one of the test chambers, and wherein the parameter associated with the plasma coagulation factor is determined from an assessed clot time for a clot formed in one or more of the test chambers; and a display contained within the system housing, the display being connected to the analyzer to receive the determined at least two hemostatic parameters and to present on a graphical user interface the determined parameters, including the parameters associated with the plasma coagulation factors, the platelets contribution, and the fibrinogen contribution, wherein the displayed plasma coagulation factors, platelets contribution, and fibrinogen contribution are used to quantify hemostatic dysfunction and direct appropriate treatment.

2. The system of claim 1, comprising a heater configured to control a temperature of the one or more blood samples.

3. The system of claim 1, wherein the piezo-actuated device comprises a piezo-electric disk, the system further comprising:

a clamp configured to press the cartridge against the receptacle to be in contact with the piezo-electric disk.

4. The system of claim 3, wherein the clamp comprises an actuator configured to move the clamp between a first position and a second position to press the cartridge against the receptacle.

5. The system of claim 1, wherein the cartridge is configured to completely seal the blood samples in the respective first, second, and third test chambers.

6. The system of claim 5, wherein the blood samples are fully drawn into the respective into the respective first, second, and third test chambers such that no air-blood interface is present therein.

7. The system of claim 1, wherein the system housing has a thickness of 17.5 cm or smaller.

8. The system of claim 7, wherein the thickness of the system housing is 2.65 cm or smaller.

9. The system of claim 1, wherein the housing of the cartridge has a thickness of 11 mm of less for each of the first, second, and third test chambers.

10. The system of claim 1, wherein the first, second, and third sets of one or more lyophilized reagents pre-loaded in the cartridge in a specified geometric region along the space of the respective first, second, and third test channels.

11. The system of claim 1, wherein the system excluding the single-use cartridge and blood samples has a weight of 10 pounds or less.

12. The system of claim 1, wherein the analyzer is configured to correct for environmental vibrations.

13. The system of claim 1, wherein the single use cartridge comprises:

a lens for each of the first, second, and third test chambers.

14. The system of claim 13, wherein each lens has one or more curved surfaces configured to form an energy focusing assembly.

15. The system of claim 13, wherein each lens comprises an integrated lens and coupling, the lens comprising a material selected from the group consisting of thermoplastic elastomer (TPE), styrene, and polystyrene.

16. The system of claim 13, wherein the analyzer further comprises one or more heating elements configured to be in communication with the single-use cartridge.

17. The system of claim 13, wherein the single use cartridge further comprises:

a filter located on an external surface of the housing, the filter being in communication with the first, second, and third test chambers and configured to allow air to pass out of the housing while retaining the sample therein when a pressure differential is subjected to the cartridge.

18. The system of claim 17, wherein the analyzer further comprises optical sensors configured to sense the filter.

19. The system of claim 13, wherein each lens and the respective first, second, and third test chambers have a combined thickness less than 19 mm.

20. The system of claim 13, wherein the single-use cartridge is formed as a die cast component.

* * * * *

UNITED STATES PATENT AND TRADEMARK OFFICE
CERTIFICATE OF CORRECTION

PATENT NO. : 11,054,396 B2
APPLICATION NO. : 15/169036
DATED : July 6, 2021
INVENTOR(S) : Francesco Viola and William F. Walker Page 1 of 1

It is certified that error appears in the above-identified patent and that said Letters Patent is hereby corrected as shown below:

In the Claims

In Column 22, Lines 35-36 of Claim 1, the text --the cartridge comprising comprises a fluid pathway-- should be --the cartridge comprising a fluid pathway--

Signed and Sealed this
Twenty-sixth Day of July, 2022

Katherine Kelly Vidal
*Director of the United States Patent and Trademark Office*